United States Patent
Yamamoto

(10) Patent No.: US 10,231,711 B2
(45) Date of Patent: Mar. 19, 2019

(54) ACOUSTIC WAVE PROCESSING DEVICE, SIGNAL PROCESSING METHOD FOR ACOUSTIC WAVE PROCESSING DEVICE, AND PROGRAM

(71) Applicant: FUJIFILM Corporation, Tokyo (JP)

(72) Inventor: Hiroaki Yamamoto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 362 days.

(21) Appl. No.: 15/228,531

(22) Filed: Aug. 4, 2016

(65) Prior Publication Data

US 2016/0338674 A1  Nov. 24, 2016

Related U.S. Application Data

(63) Continuation of application No. PCT/JP2014/077292, filed on Oct. 14, 2014.

(30) Foreign Application Priority Data

Mar. 25, 2014  (JP) .................................. 2014-062563

(51) Int. Cl.
*A61B 8/14* (2006.01)
*A61B 8/08* (2006.01)
(Continued)

(52) U.S. Cl.
CPC .............. *A61B 8/5207* (2013.01); *A61B 8/14* (2013.01); *A61B 8/4444* (2013.01);
(Continued)

(58) Field of Classification Search
CPC ..... A61B 8/5207; A61B 8/4488; A61B 8/461; A61B 8/4444; A61B 8/54; A61B 8/4483;
(Continued)

(56) References Cited

U.S. PATENT DOCUMENTS 5,295,485 A    3/1994  Shinomura et al.
6,213,945 B1 *  4/2001  Tynan .................... A61B 8/06
                                                                600/441
(Continued)

FOREIGN PATENT DOCUMENTS

JP       5-161641 A     6/1993
JP    2009-536853 A    10/2009
(Continued)

OTHER PUBLICATIONS

International Search Report (PCT/ISA/210) for PCT/JP2014/077292 dated Dec. 2, 2014.
(Continued)

*Primary Examiner* — Sanjay Cattungal
(74) *Attorney, Agent, or Firm* — Birch Stewart Kolasch & Birch, LLP

(57) ABSTRACT

The acoustic wave processing device includes a phasing addition unit which performs phasing addition on respective pieces of first element data with different elements as a reference to generate a plurality of pieces of first reception data, a reception data storage unit which stores first reception data, a reception data generation unit which superimposes two or more pieces of first reception data to generate second reception data, and a processing condition setting unit which sets the number of times of superimposition of first reception data. In a cine-reproduction mode, the reception data generation unit superimposes the set number of pieces of first reception data to generate second reception data.

20 Claims, 9 Drawing Sheets

(51) Int. Cl.
  *G01S 7/52* (2006.01)
  *G01S 15/89* (2006.01)
  *G10K 11/34* (2006.01)
  *A61B 8/00* (2006.01)

(52) U.S. Cl.
  CPC .......... *A61B 8/4483* (2013.01); *A61B 8/4488* (2013.01); *A61B 8/461* (2013.01); *A61B 8/5253* (2013.01); *A61B 8/54* (2013.01); *G01S 7/52047* (2013.01); *G01S 7/52095* (2013.01); *G01S 15/8915* (2013.01); *G10K 11/346* (2013.01); *A61B 8/469* (2013.01)

(58) Field of Classification Search
  CPC ......... A61B 8/14; A61B 8/5253; A61B 8/469; G01S 7/52095; G01S 7/52047; G01S 15/8915; G10K 11/346
  See application file for complete search history.

(56) References Cited

U.S. PATENT DOCUMENTS

| | | | |
|---|---|---|---|
| 9,177,110 B1* | 11/2015 | Fram | G06F 19/321 |
| 2004/0267122 A1* | 12/2004 | Nadadur | A61B 8/08 600/440 |
| 2007/0016029 A1* | 1/2007 | Donaldson | A61B 5/7475 600/437 |
| 2009/0182235 A1 | 7/2009 | Robert et al. | |
| 2012/0004545 A1 | 1/2012 | Ziv-Ari et al. | |
| 2012/0078097 A1* | 3/2012 | Wang | A61B 8/483 600/437 |
| 2013/0345563 A1* | 12/2013 | Stuebe | G01S 7/52084 600/440 |
| 2015/0141831 A1 | 5/2015 | Yamamoto | |
| 2016/0173770 A1* | 6/2016 | Fosodeder | A61B 8/5207 348/77 |
| 2017/0124701 A1* | 5/2017 | Liang | A61B 8/0858 |

FOREIGN PATENT DOCUMENTS

| | | |
|---|---|---|
| JP | 2012-11193 A | 1/2012 |
| JP | 2014-30715 A | 2/2014 |

OTHER PUBLICATIONS

Written Opinion of the International Searching Authority (PCT/ISA/237) for PCT/JP2014/077292 dated Dec. 2, 2014.

Japanese Office Action for Japanese Application No. 2014-062563, dated Nov. 1, 2016, with a machine translation.

English Translation of International Preliminary Report on Patentability (including PCT/IB/373 and PCT/ISA/237) for PCT/JP2014/077292, dated Sep. 27, 2016.

* cited by examiner

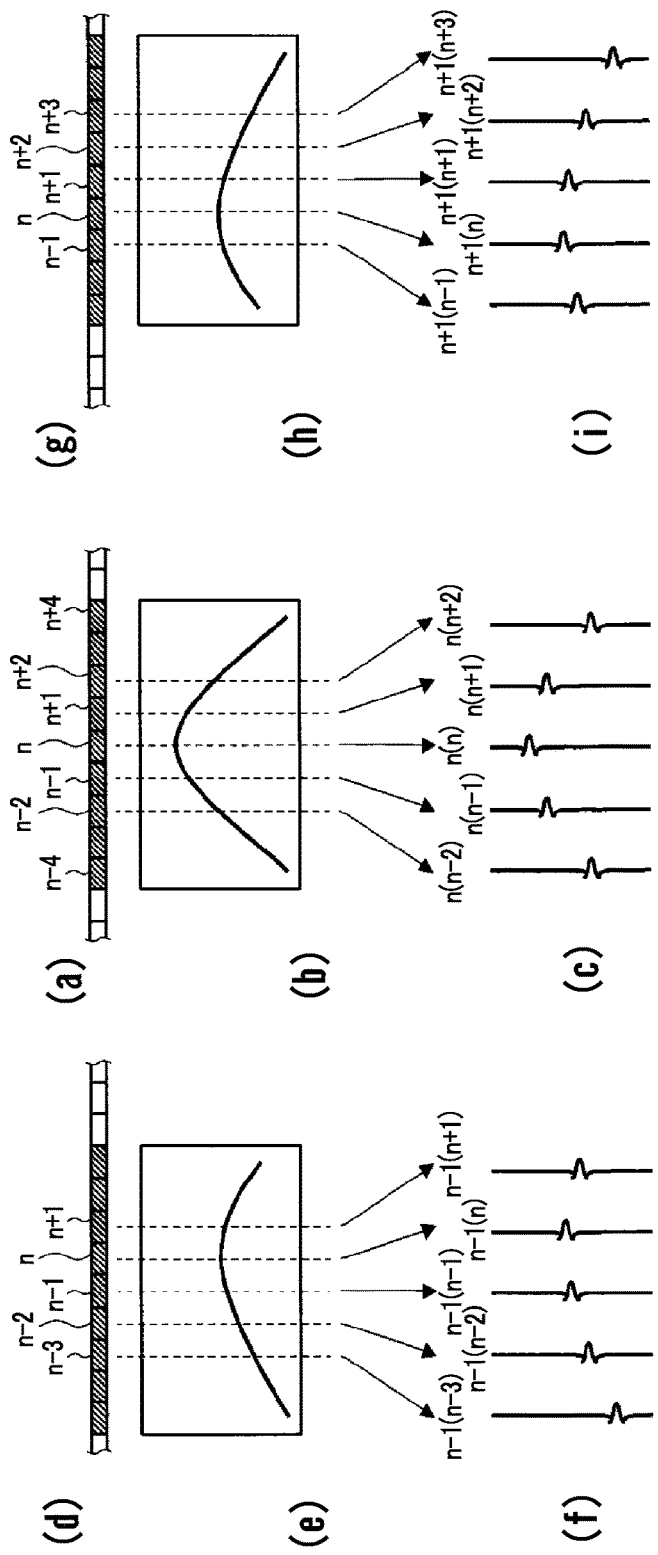

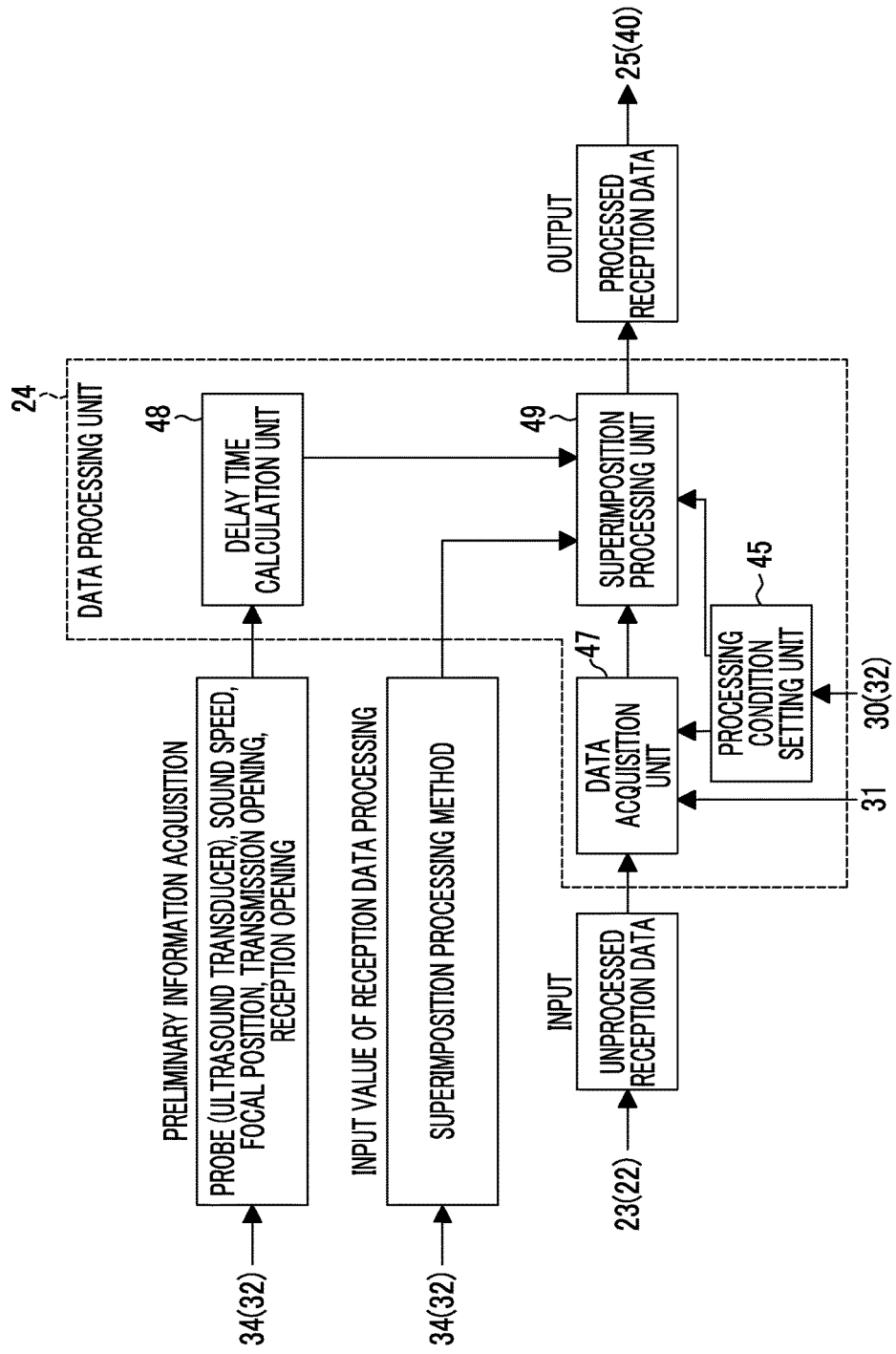

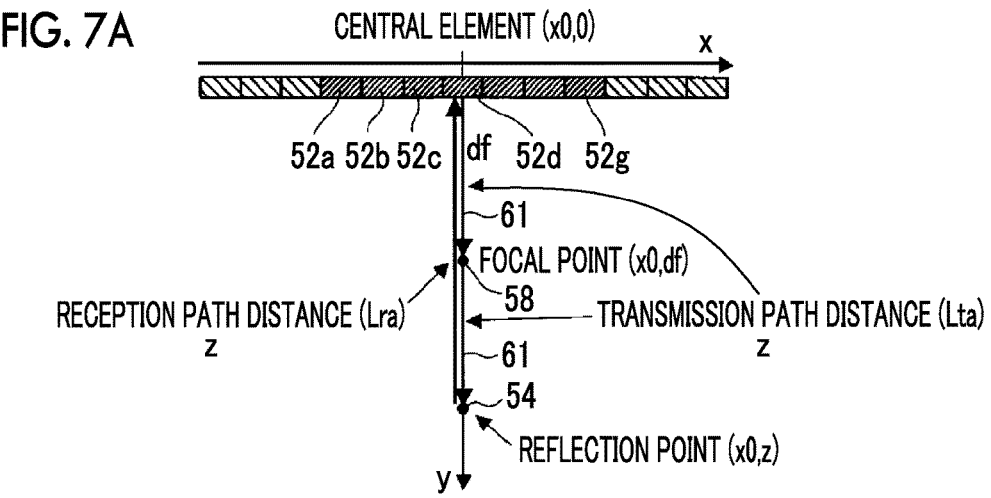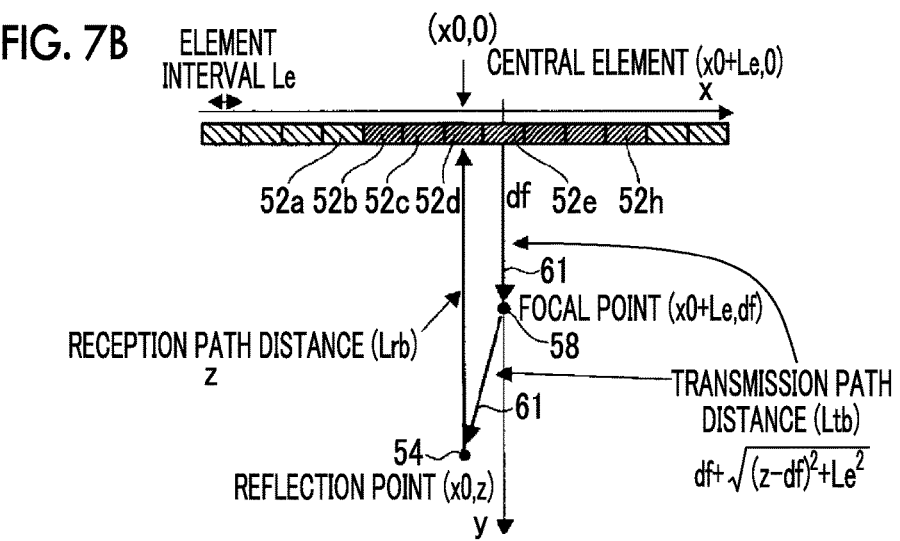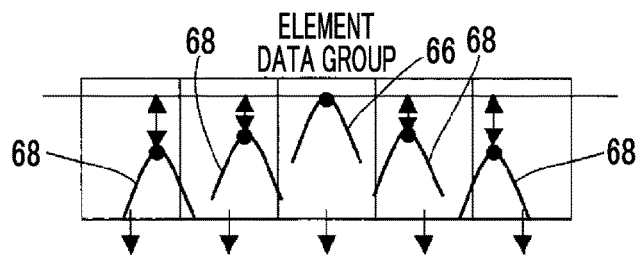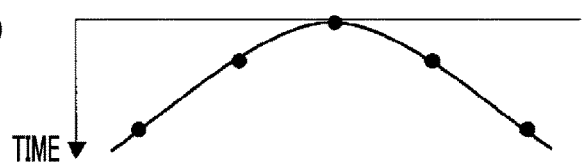

ACOUSTIC WAVE PROCESSING DEVICE, SIGNAL PROCESSING METHOD FOR ACOUSTIC WAVE PROCESSING DEVICE, AND PROGRAM

CROSS-REFERENCE TO RELATED APPLICATIONS

This application is a Continuation of PCT International Application No. PCT/JP2014/077292 filed on Oct. 14, 2014, which claims priority under 35 U.S.C § 119 (a) to Japanese Patent Application No. 2014-062563 filed on Mar. 25, 2014. Each of the above application(s) is hereby expressly incorporated by reference, in its entirety, into the present application.

BACKGROUND OF THE INVENTION

1. Field of the Invention

The present invention relates to an acoustic wave processing device, a signal processing method, and a non-transitory computer readable recording medium storing a program which transmit and receive an acoustic beam to capture an image of an object to be inspected, such as an organ in a living body, and generate an acoustic image or the like for inspection and diagnosis of the object to be inspected.

2. Description of the Related Art

Hitherto, an acoustic diagnostic apparatus, such as an ultrasound image diagnostic apparatus, which generates an ultrasound image for inspection or diagnosis of an object to be inspected using an acoustic wave, such as an ultrasonic wave has come into practical use in a medical field.

In general, this kind of ultrasound diagnostic apparatus has an ultrasound probe (hereinafter, referred to as a probe) embedded with a plurality of elements (ultrasound transducers), and an apparatus body connected to the probe. In the ultrasound diagnostic apparatus, an ultrasound beam is transmitted from a plurality of elements of the probe toward a subject (object to be inspected) so as to form a predetermined focal point (transmission foal point), an ultrasonic echo from the subject is received by the probe, and the reception signal of the received ultrasonic echo is electrically processed by the apparatus body to generate an ultrasound image.

In the ultrasound diagnostic apparatus, scanning of ultrasonic waves is performed to generate ultrasound images, and the generated ultrasound images are sequentially displayed on a display unit in real time; however, there is a requirement to observe the ultrasound image again for diagnosis after such inspection. For this reason, in the ultrasound diagnostic apparatus, the generated ultrasound images are stored, and in a case where a cine-reproduction mode is selected, the stored ultrasound images are reproduced.

Received wave signal data (element data) is stored, and in the cine-reproduction mode, image data is generated again from the stored element data (JP1993-161641A (JP-H05-161641A). If the conditions for creating an image in the cine-reproduction mode are changed, it is thereby possible to change the image quality of the ultrasound image in the cine-reproduction mode to be different from the ultrasound image generated in real time, and for example, to obtain a higher-image quality ultrasound image.

The ultrasound beam drives a plurality of elements based on a predetermined transmission delay pattern and is transmitted so as to form the set focal point. This ultrasound beam has a shape having a width in a transverse direction. For this reason, there is a problem in that information of a reflection point at a position shifted in a transverse direction is picked up, and is reproduced on the ultrasound image as a so-called ghost signal.

In regard to this problem, in the ultrasound diagnostic apparatus, so-called multiline processing in which a plurality of pieces of data (element data or reception data) obtained by each transmission are superimposed according to the reception time or the position of the element to correct data in the generation of one ultrasound image (JP2009-536853A). In a case of ghost signals, even if the pieces of data are superimposed according to the reception time or the position of the element, ghost signals are superimposed in a shifted state and cancel each other; thus, it is possible to remove the ghost signals.

SUMMARY OF THE INVENTION

However, since element data is very large in volume, it is difficult to store element data for many frames for cine-reproduction.

In a device which performs multiline processing to generate an ultrasound image, in a case where element data is stored and an ultrasound image is reproduced in a cine-reproduction mode, in order to generate an ultrasound image from element data, it is necessary to perform multiline processing many times. For this reason, there is a problem in that a calculation time is increased, and a long time is required for reproduction.

The invention has been accomplished in order to solve the problems in the related art, and an object of the invention is to provide an acoustic wave processing device, a signal processing method, and a non-transitory computer readable recording medium storing a program capable of reducing the amount of data to be stored for cine-reproduction, reducing a calculation time at the time of cine-reproduction, and obtaining an ultrasound image of a different image quality from a real-time ultrasound image in an acoustic wave processing device which performs multiline processing.

The inventors have intensively studied in order to attain the above-described object and have found that the above-described problems can be solved by providing a phasing addition unit which performs phasing addition on the respective pieces of first element data with at least two elements as a reference to generate at least two pieces of first reception data for each piece of first element data, a reception data storage unit which stores a plurality of pieces of first reception data generated in the phasing addition unit, a data acquisition unit which reads two or more pieces of first reception data from the plurality of pieces of first reception data stored in the reception data storage unit, a reception data generation unit which superimposes the two or more pieces of first reception data read by the data acquisition unit to generate second reception data, and a processing condition setting unit which sets the number of pieces of first reception data for use when generating the second reception data in the reception data generation unit, and in the cine-reproduction mode, by making the data acquisition unit read the first reception data, the number of pieces of which is set by the processing condition setting unit, from the reception data storage unit and the reception data generation unit superimpose the read first reception data to generate the second reception data.

That is, the invention provides (1) to (11) described below.

(1) An acoustic wave processing device comprising a probe which has a plurality of elements arranged to transmit an acoustic beam, to receive an acoustic echo reflected from an object to be inspected, and to output an analog element signal according to the received acoustic echo, a transmission unit which uses two or more elements among the plurality of elements as a transmission element and makes the probe transmit the acoustic beam multiple times so as to form a predetermined transmission focal point, a reception unit which receives an acoustic echo corresponding to each transmission of the acoustic beam with two or more elements among the plurality of elements as a reception element, receives analog element signals output from the reception elements, and performs predetermined processing on the analog element signals, an A/D conversion unit which performs A/D conversion on the analog element signals processed by the reception unit to convert the analog element signals to first element data as a digital element signal, a phasing addition unit which performs phasing addition on the respective pieces of first element data with at least two elements as a reference to generate at least two pieces of first reception data for each piece of first element data, a reception data storage unit which stores a plurality of pieces of first reception data generated in the phasing addition unit, a data acquisition unit which reads two or more pieces of first reception data from the plurality of pieces of first reception data stored in the reception data storage unit, a reception data generation unit which superimposes the two or more pieces of first reception data read by the data acquisition unit to generate second reception data, a processing condition setting unit which sets the number of pieces of first reception data for use when generating the second reception data in the reception data generation unit, and a mode switching unit which switches between a measurement mode for performing transmission and reception of the acoustic wave and reproducing an image based on the received acoustic echo and a cine-reproduction mode for generating and reproducing an image using the plurality of pieces of first reception data stored in the reception data storage unit without performing transmission and reception of the acoustic wave, wherein, in the cine-reproduction mode, the data acquisition unit reads the first reception data, the number of pieces of which is set by the processing condition setting unit, from the reception data storage unit, and the reception data generation unit superimposes the read first reception data to generate the second reception data.

(2) The acoustic wave processing device described in (1), wherein the data acquisition unit reads the two or more pieces of first reception data generated from different pieces of first element data and generated through phasing addition with the same element as a reference from the plurality of pieces of first reception data stored in the reception data storage unit.

(3) The acoustic wave processing device described in (1) or (2), wherein the reception data generation unit superimposes the two or more pieces of first reception data read by the data acquisition unit according to a reception time of an acoustic echo received by each element to generate the second reception data.

(4) The acoustic wave processing device described in any one of (1) to (3), wherein the reception data generation unit superimposes two or more pieces of first reception data to generate the second reception data in the measurement mode, and the number of times of phasing addition which is performed on one piece of first reception data in the phasing addition unit is greater than the number of times of superimposition in the reception data generation unit in the measurement mode.

(5) The acoustic wave processing device described in any one of (1) to (4), wherein the reception data generation unit superimposes two or more pieces of first reception data to generate the second reception data in the measurement mode, and the number of times of superimposition of the first reception data in the reception data generation unit in the cine-reproduction mode is greater than the number of times of superimposition in the reception data generation unit in the measurement mode.

(6) The acoustic wave processing device described in any one of (1) to (5), wherein the number of times of phasing addition which is performed on one piece of first reception data in the phasing addition unit is set according to the width of the acoustic beam.

(7) The acoustic wave processing device described in any one of (1) to (6), wherein the transmission unit performs at least one of change of a central element or change of a transmission direction of an acoustic beam to make the probe transmit the acoustic beam multiple times.

(8) The acoustic wave processing device described in any one of (1) to (7), wherein the reception data generation unit applies weighting to the two or more pieces of first reception data and superimposes the two or more pieces of first reception data to generate the second reception data.

(9) The acoustic wave processing device described in any one of (1) to (8), further comprising an operating unit which receives an input instruction for setting the number of times of superimposition in the reception data generation unit, wherein the reception data generation unit superimposes the first reception data based on the input instruction from the operating unit to generate the second reception data.

(10) A signal processing method for an acoustic wave processing device, which inspects an object to be inspected using a probe having a plurality of elements arranged to transmit an acoustic beam, to receive an acoustic echo reflected from the object to be inspected, and to output an analog element signal according to the received acoustic echo, the signal processing method comprising a transmission step of using two or more elements among the plurality of elements of the probe as a transmission element and making the probe transmit the acoustic beam multiple times so as to form a predetermined transmission focal point, a reception time of receiving an acoustic echo corresponding to each transmission of the acoustic beam with two or more elements among the plurality of elements as a reception element and outputting an analog element signal, an A/D conversion step of performing A/D conversion on the analog element signal to generate first element data as a digital element signal, a phasing addition step of performing phasing addition on the respective pieces of generated first element data with at least two elements as a reference to generate at least two pieces of first reception data for each piece of first element data, a reception data storage step of storing a plurality of pieces of first reception data generated in the phasing addition step, a data acquisition step of reading two or more pieces of first reception data from the plurality of pieces of first reception data stored in the reception data storage step, a reception data generation step of superimposing the two or more pieces of first reception data read in the data acquisition step to generate second reception data, a processing condition setting step of setting the number of pieces of first reception data for use when generating the second reception data in the reception data generation step, and a mode switching step of switching between a measurement mode for performing transmission and reception of the acoustic wave and reproducing an image based on the received acoustic echo and a cine-reproduction mode for generating and reproducing an image using the plurality of pieces of first reception data stored in the reception data storage unit without performing transmission and reception of the acoustic wave, wherein, in the cine-reproduction mode, the first reception data, the number of pieces of which is set in the processing condition setting step, is read from the reception data storage unit in the data acquisition step, and the read first reception data is superimposed to generate the second reception data in the reception data generation step.

(11) A non-transitory computer readable recording medium storing a program which causes a computer to execute a signal processing method for an acoustic wave processing device, which inspects an object to be inspected using a probe having a plurality of elements arranged to transmit an acoustic beam, to receive an acoustic echo reflected from the object to be inspected, and to output an analog element signal according to the received acoustic echo, the program causing the computer to execute a transmission step of using two or more elements among the plurality of elements of the probe as a transmission element and making the probe transmit the acoustic beam multiple times so as to form a predetermined transmission focal point, a reception time of receiving an acoustic echo corresponding to each transmission of the acoustic beam with two or more elements among the plurality of elements as a reception element and outputting an analog element signal, an A/D conversion step of performing A/D conversion on the analog element signal to generate first element data as a digital element signal, a phasing addition step of performing phasing addition on the respective pieces of generated first element data with at least two lines as a center to generate at least two pieces of first reception data for each piece of first element data, a reception data storage step of storing a plurality of pieces of first reception data generated in the phasing addition step, a data acquisition step of reading two or more pieces of first reception data from the plurality of pieces of first reception data stored in the reception data storage step, a reception data generation step of superimposing the two or more pieces of first reception data read in the data acquisition step to generate second reception data, a processing condition setting step of setting the number of pieces of first reception data for use when generating the second reception data in the reception data generation step, and a mode switching step of switching between a measurement mode for performing transmission and reception of the acoustic wave and reproducing an image based on the received acoustic echo and a cine-reproduction mode for generating and reproducing an image using the plurality of pieces of first reception data stored in the reception data storage unit without performing transmission and reception of the acoustic wave, wherein, in the cine-reproduction mode, the first reception data, the number of pieces of which is set in the processing condition setting step, is read from the reception data storage unit in the data acquisition step, and the read first reception data is superimposed to generate the second reception data in the reception data generation step.

According to the invention, it is possible to provide an acoustic wave processing device, a signal processing method, and a non-transitory computer readable recording medium storing a program capable of reducing the amount of data to be stored for cine-reproduction, reducing a calculation time at the time of cine-reproduction, and obtaining an ultrasound image of a different image quality from a real-time ultrasound image in an acoustic wave processing device which performs multiline processing.

Parts (a), (d), and (g) of FIG. 3 are conceptual diagrams illustrating respective reception elements, parts (b), (e), and (h) of FIG. 3 are conceptual diagrams showing element data obtained by transmission and reception of ultrasonic waves, and parts (c), (f), and (i) of FIG. 3 are conceptual diagrams showing unprocessed reception data obtained by performing phasing addition processing on respective pieces of element data.

Figure 1:
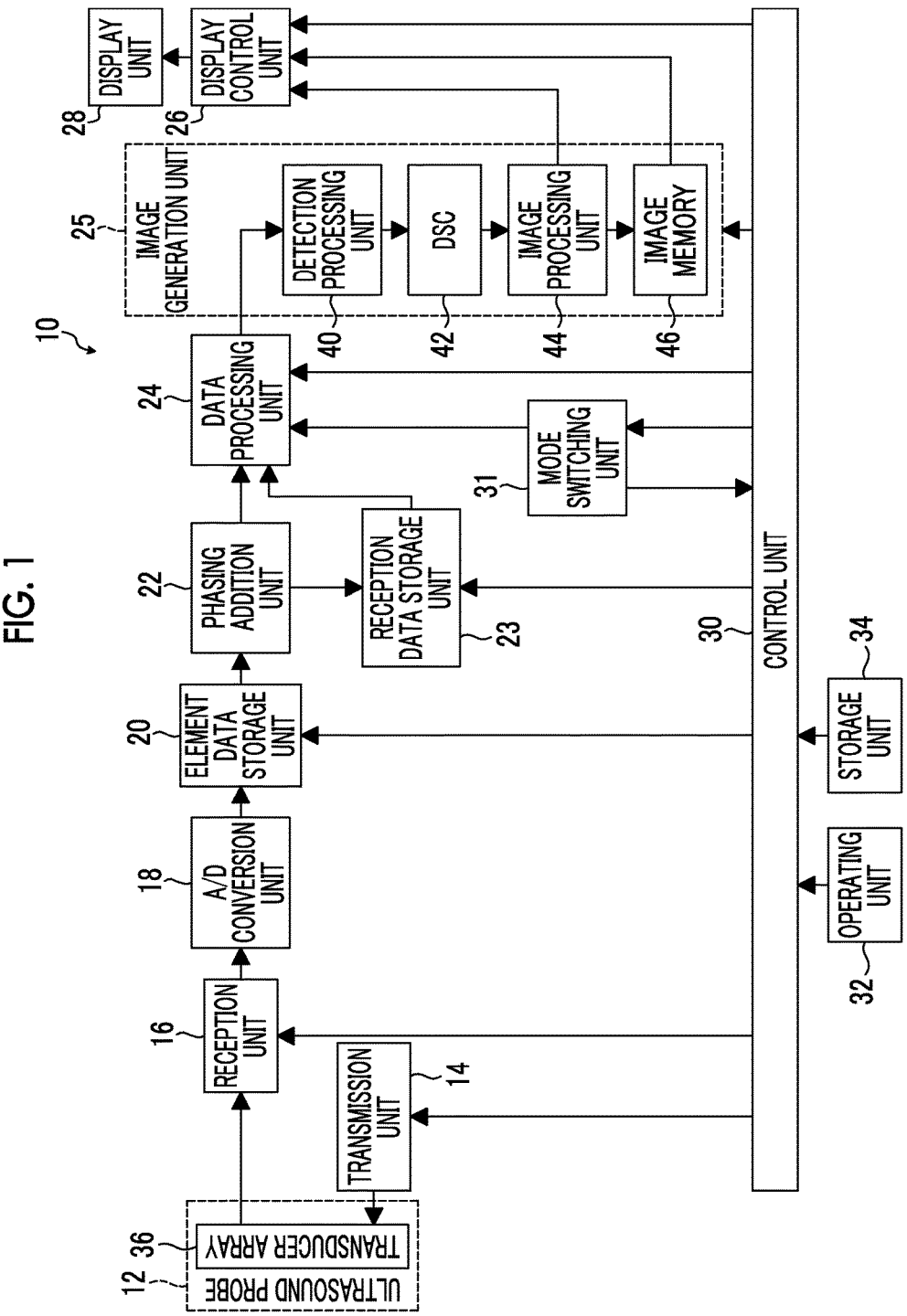
FIG. 1 is a block diagram conceptually showing an example of the configuration of an ultrasound diagnostic apparatus of the invention.

FIG. 4 is a block diagram conceptually showing an example of the configuration of a data processing unit of the ultrasound diagnostic apparatus shown in FIG. 1.

Figure 5B:
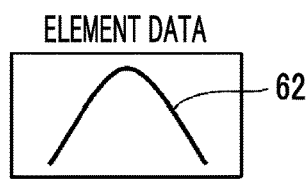
Figure 5D:
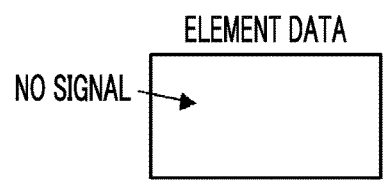
Figure 5A:
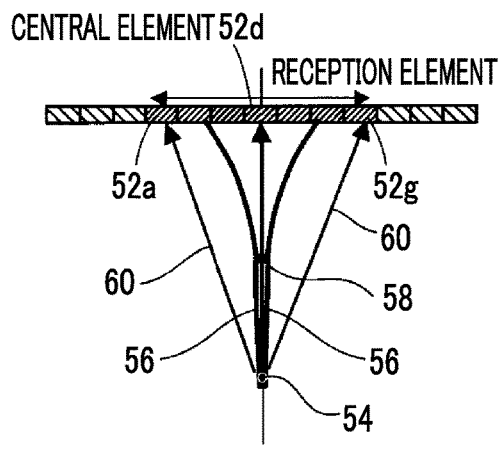
Figure 5C:
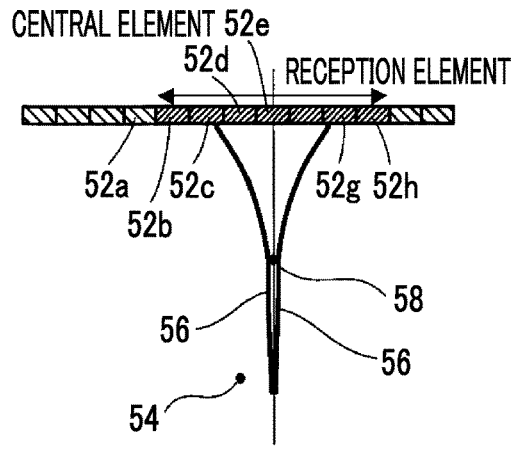

FIGS. 5A and 5C are conceptual diagrams illustrating transmission and reception of ultrasonic waves by an ideal ultrasound beam, and FIGS. 5B and 5D are conceptual diagrams showing element data obtained by transmission and reception of ultrasonic waves.

Figure 6B:
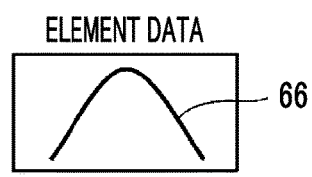
Figure 6D:
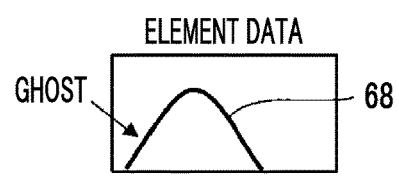
Figure 6A:
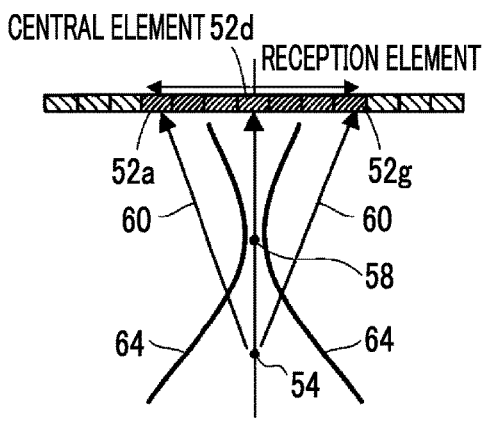
Figure 6C:
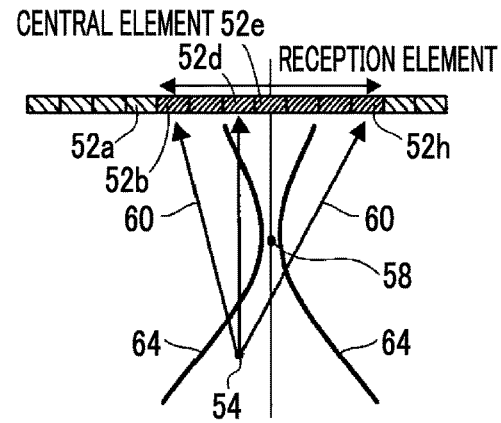

FIGS. 6A and 6C are conceptual diagrams illustrating transmission and reception of ultrasonic waves by an actual ultrasound beam, and FIGS. 6B and 6D are conceptual diagrams showing element data obtained by transmission and reception of ultrasonic waves.

FIGS. 7A and 7B are conceptual diagrams illustrating a path of sonic waves in a case where transmission and reception of ultrasonic waves by different central elements are performed for the same reflection point, FIG. 7C is a conceptual diagram of element data obtained by a plurality of elements, and FIG. 7D is a conceptual diagram illustrating a delay time of element data shown in FIG. 7C.

Figure 8:
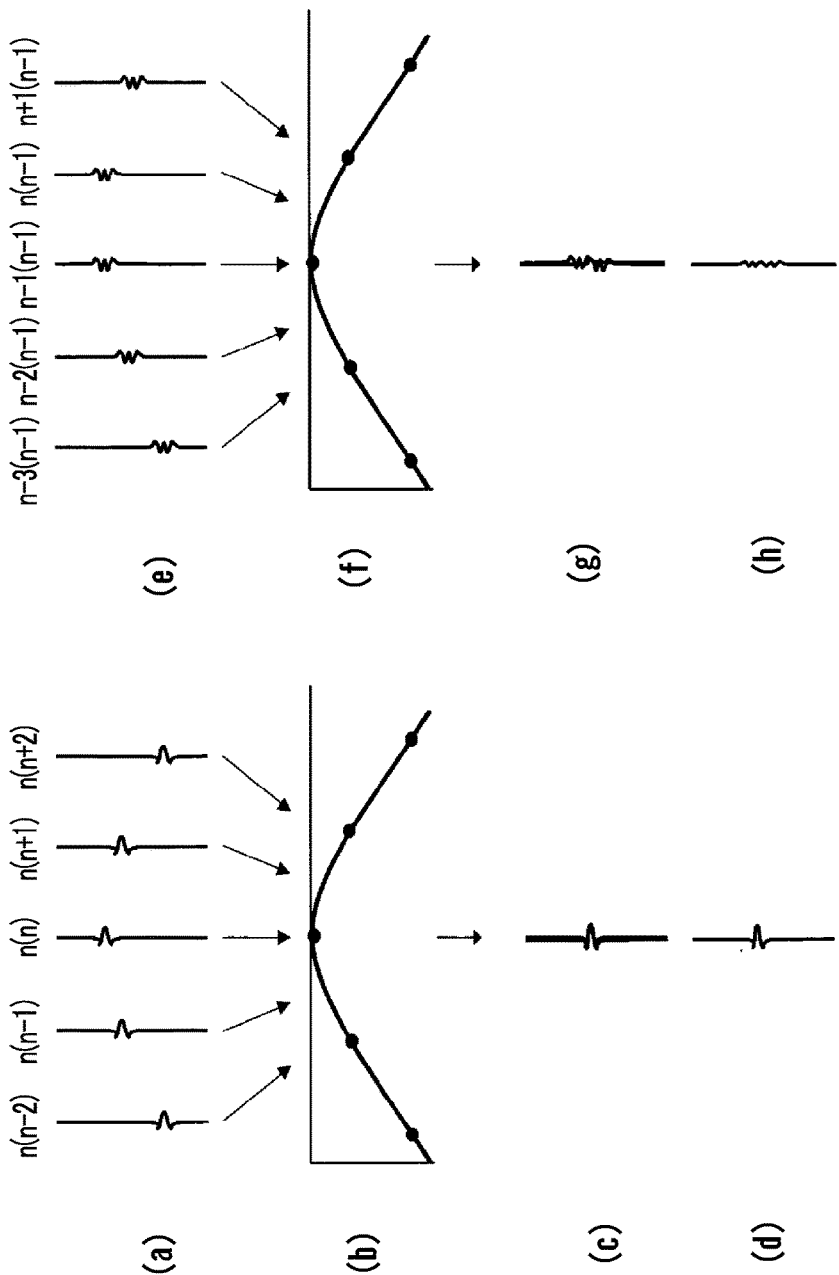

Parts (a) and (e) of FIG. 8 are conceptual diagrams showing unprocessed reception data to be superimposed, parts (b) and (f) of FIG. 8 are conceptual diagrams illustrating a delay time of unprocessed reception data, parts (c) and (g) of FIG. 8 are conceptual diagrams illustrating a state of superimposition of unprocessed reception data, and parts (d) and (h) of FIG. 8 are conceptual diagrams illustrating a result of superimposition of unprocessed reception data.

Figure 9A:
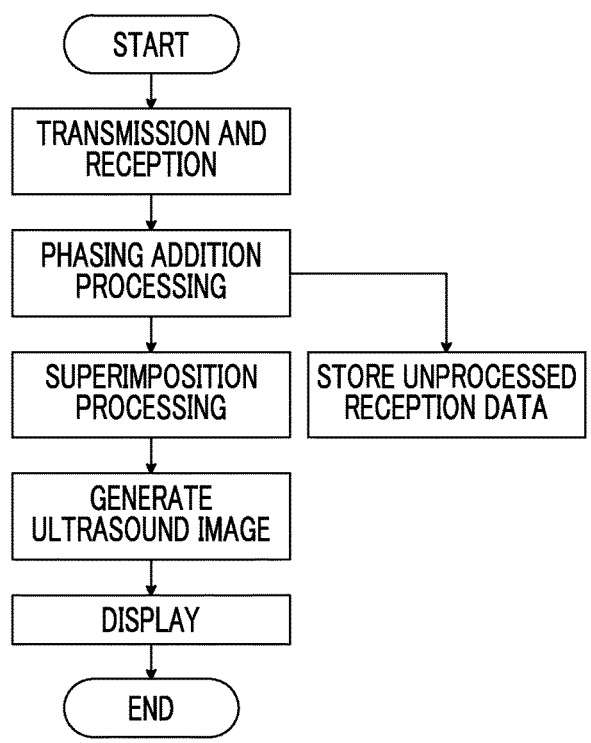
Figure 9B:
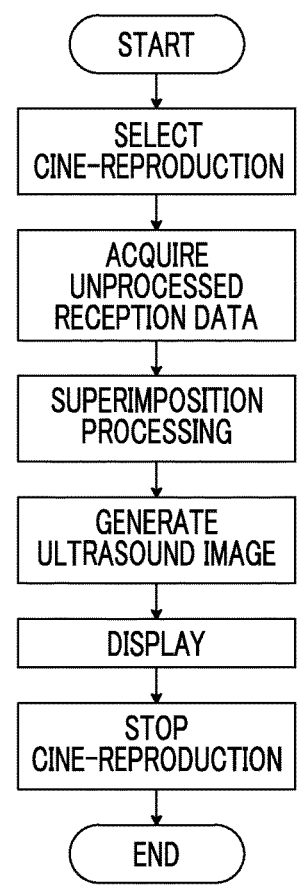

FIGS. 9A and 9B are flowcharts illustrating the action of the ultrasound diagnostic apparatus shown in FIG. 1.

DESCRIPTION OF THE PREFERRED EMBODIMENTS

Hereinafter, an acoustic wave processing device, a signal processing method, and a program of the invention will be described in detail based on a preferred first embodiment shown in the accompanying drawings.

In the embodiment of the invention, although an ultrasonic wave is used as an acoustic wave, the invention is not limited to the ultrasonic wave, and an acoustic wave of an audio frequency may be used if an appropriate frequency is selected according to a target to be inspected, measurement conditions, or the like.

FIG. 1 conceptually shows an example of an ultrasound diagnostic apparatus (acoustic wave processing device) of the invention using a block diagram.

As shown in FIG. 1, an ultrasound diagnostic apparatus 10 has an ultrasound probe 12, a transmission unit 14 and a reception unit 16 connected to the ultrasound probe 12, an A/D conversion unit 18, an element data storage unit 20, a phasing addition unit 22, a reception data storage unit 23, a data processing unit 24, an image generation unit 25, a display control unit 26, a display unit 28, a control unit 30, a mode switching unit 31, an operating unit 32, and a storage unit 34.

In the example of the drawing, the transmission unit 14, the reception unit 16, the A/D conversion unit 18, the element data storage unit 20, the phasing addition unit 22, the reception data storage unit 23, the data processing unit 24, the image generation unit 25, the display control unit 26, the display unit 28, the control unit 30, the mode switching unit 31, the operating unit 32, and the storage unit 34 constitute an apparatus body of the ultrasound diagnostic apparatus 10.

The ultrasound probe 12 is a known ultrasound probe which is used in a typical ultrasound diagnostic apparatus.

The ultrasound probe 12 (hereinafter, referred to as a probe 12) has a transducer array 36 in which ultrasound transducers are arranged in a one-dimensional or two-dimensional manner.

The ultrasound transducer transmits an ultrasound beam to a subject in response to a drive signal supplied from the transmission unit 14 when capturing an ultrasound image of an object to be inspected (hereinafter, referred to as a subject), receives an ultrasonic echo reflected from the subject, and outputs a reception signal according to the strength of the received ultrasonic wave.

Each ultrasound transducer is constituted of a transducer in which electrodes are formed at both ends of a piezoelectric substance made of, for example, piezoelectric ceramic represented by Pb (lead) zirconate titanate (PZT), a polymer piezoelectric element represented by polyvinylidene fluoride (PVDF), piezoelectric single crystal represented by a magnesium niobate-lead titanate solid solution (PMN-PT), or the like.

If a pulsed or continuous-wave voltage is applied to the electrodes of each of the transducers, the piezoelectric substance expands and contracts according to the applied voltage, and a pulsed or continuous-wave ultrasonic wave is generated from each transducer. The ultrasonic waves generated from the respective transducers are converged on a set focal point according to the delay of drive of each transducer and synthesized (that is, transmission-focused) to form an ultrasound beam.

The transducers expand and contract when the ultrasonic echo reflected from the inside of the subject enters, and electrical signals according to the magnitude of expansion and contraction are generated. The electrical signals are output to the reception unit 16 as reception signals (analog element signals).

The transmission unit 14 has, for example, a plurality of pulsers, and supplies a drive signal (applies a drive voltage) to the respective ultrasound transducers of the probe 12.

The transmission unit 14 performs transmission focusing for adjusting the delay amount of the drive signal (the application timing of the drive voltage) based on a transmission delay pattern selected by the control unit 30 such that ultrasonic waves transmitted from a predetermined number (a plurality) of ultrasound transducers (transmission elements) form an ultrasound beam converged on the set focal point, and supplies the drive signal to the ultrasound transducers.

With this, an intended ultrasound beam is transmitted from the probe 12 (transducer array 36) to the subject.

The reception unit 16 receives the reception signals output from a predetermined number (a plurality) of ultrasound transducers (reception elements) corresponding to the single transmission of an ultrasound beam in response to a control signal from the control unit 30, performs predetermined processing, such as amplification, on the reception signals, and supplies the reception signals to the A/D conversion unit 18.

In the ultrasound diagnostic apparatus 10 of the invention, a method of transmitting and receiving an ultrasonic wave is basically the same as that in a known ultrasound diagnostic apparatus.

Accordingly, in the single transmission and reception of an ultrasonic wave (transmission of one ultrasound beam and reception of an ultrasonic echo corresponding to the transmission), the number of ultrasound transducers (the number of transmission openings) which generate ultrasonic waves and the number of ultrasound transducers (the number of reception openings) which receive ultrasonic waves (the reception unit 16 receives the reception signals) are not limited as long as the number of ultrasound transducers is plural. In the single transmission and reception, the number of openings may be the same or different between transmission and reception.

In adjacent ultrasound beams in at least an azimuth direction (the arrangement direction of the ultrasound transducers), if transmission regions overlap each other, the number of transmissions and receptions of an ultrasonic wave (the number of sound rays) for forming one ultrasound image or the interval of ultrasound transducers (central elements) to be the center of transmission and reception (that is, the density of scan lines/sound rays) is not limited. Accordingly, transmission and reception of an ultrasonic wave may be performed with all ultrasound transducers corresponding to a region scanned using an ultrasonic wave as a central element, or transmission and reception of an ultrasonic wave may be performed with ultrasound transducers at predetermined intervals, for example, at every two or every four ultrasound transducers, as a central element.

Similarly to a known ultrasound diagnostic apparatus, in order to form one ultrasound image, transmission and reception are performed at a plurality of positions (lines) while sequentially moving the transmission and reception positions.

The A/D conversion unit 18 performs analog/digital conversion on the analog reception signals supplied from the reception unit 16 to element data (first element data) as digital reception signals.

The A/D conversion unit 18 supplies the A/D-converted element data to the element data storage unit 20.

The element data storage unit 20 sequentially stores element data supplied from the A/D conversion unit 18. The element data storage unit 20 stores information (for example, the depth of a reflection position of an ultrasonic wave, the density of scan lines, and a parameter indicating a visual field width) relating to a frame rate input from the control unit 30 in association with the respective pieces of element data.

Preferably, the element data storage unit 20 stores all pieces of element data corresponding to at least one ultrasound image (an ultrasound image of one frame) and does not erase element data of the ultrasound image during display and before display until at least the display of the ultrasound image ends.

The phasing addition unit 22 is a unit which performs phasing addition processing per element data under the control of the control unit 30 with two or more different elements (ultrasound transducers) as a reference to generate two or more pieces of unprocessed reception data (first reception data) for each piece of element data.

In the following description, the ultrasound transducers are also simply referred to as "elements".

Hereinafter, the phasing addition processing which is performed in the phasing addition unit 22 will be described.

As described above, the transducer array 36 of the probe 12 has a plurality of elements (ultrasound transducers) arranged in a one-dimensional or two-dimensional manner. Accordingly, the distance to one reflection point in the subject is different by ultrasound transducer. For this reason, even in an ultrasonic echo reflected at the same reflection point, the time at which the ultrasonic echo reaches each ultrasound transducer is different. The phasing addition unit 22 delays each signal of element data by an amount corresponding to the difference (delay time) in the reaching time of the ultrasonic echo in the respective ultrasound transducers according to a reception delay pattern selected by the control unit 30, performs reception focusing processing in a digital manner by performing phasing addition element data assigned with the delay time, and generates reception data.

Figure 2:
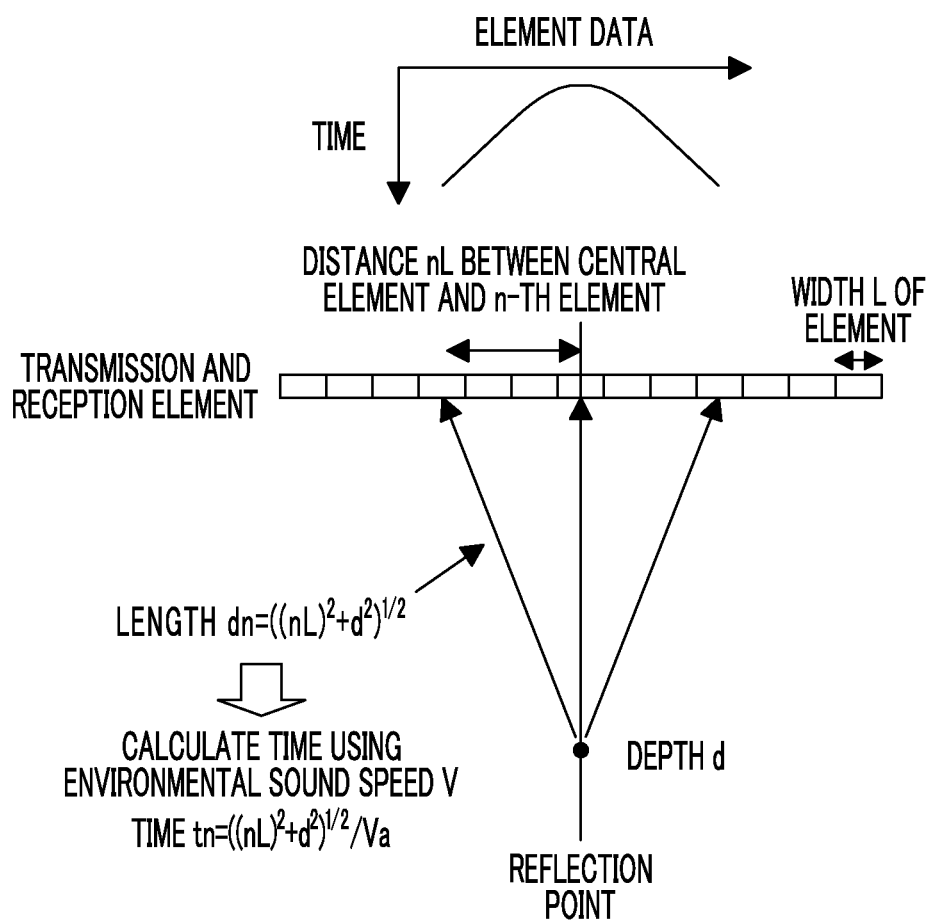
FIG. 2 is a conceptual diagram illustrating an example of reception focusing processing in the ultrasound diagnostic apparatus shown in FIG. 1.

FIG. 2 shows an example of the reception focusing processing.

FIG. 2 shows a case of a linear probe in which a plurality of ultrasound transducers of the probe 12 are arranged in a line in a right-left direction of the drawing. However, in a case of a convex probe, the probe shape is different, but a way of thinking may be the same.

FIG. 2 shows an example where the reception focusing processing is performed with a central ultrasound transducer as a reference, that is, a line of a central ultrasound transducer as a reference line.

If the width of each ultrasound transducer in the azimuth direction is L, the distance between the central ultrasound transducer in the azimuth direction and an n-th ultrasound transducer toward an end portion becomes nL.

As shown in the drawing, if a reflection point of an ultrasonic wave is positioned at a distance (depth) d vertical to the arrangement direction from the central ultrasound transducer, the distance (length) $d_n$, between the n-th ultrasound transducer and the reflection point is calculated by Expression (1).

$$d_n = ((nL)^2 + d^2)^{1/2} \quad (1)$$

Accordingly, the time $t_n$, at which an ultrasonic echo reaches (is received by) the n-th ultrasound transducer from the reflection point is calculated by Expression (2) using a sound speed (environmental sound speed) Va of an ultrasonic wave in the subject.

$$t_n = d_n/Va = ((nL)^2 + d^2)^{1/2}/Va \quad (2)$$

As described above, the distance between the ultrasound transducer and the reflection point is different for each ultrasound transducer. For this reason, in this example, as shown in a graph on the upper side of the drawing, the reaching time $t_n$, of the ultrasonic echo becomes longer as the ultrasound transducer is closer to the end portion in the arrangement direction.

Specifically, if the time until an ultrasonic wave is received by the central ultrasound transducer from the reflection point is $t_1$, an ultrasonic wave received by the n-th ultrasound transducer is delayed by the time $\Delta t = t_n - t_1$ with respect to an ultrasonic wave received by the central ultrasound transducer. In this example, the delay time At is, that is, a reception delay pattern.

The phasing addition unit 22 performs phasing addition on the signals corresponding to the respective ultrasound transducers using the delay time represented by the time $\Delta t$ and performs reception focusing processing to generate unprocessed reception data.

As described above, the phasing addition unit 22 performs the reception focusing processing on one piece of element data multiple times while changing an element to be a reference, that is, a reference line, and generates two or more pieces of unprocessed reception data for each piece of element data.

This will be described referring to parts (a) to (i) of FIG. 3.

Parts (a), (d), and (g) of FIG. 3 are conceptual diagrams illustrating respective reception elements, parts (b), (e), and (h) of FIG. 3 are conceptual diagrams showing element data obtained by transmission and reception of ultrasonic waves, and parts (c), (f), and (i) of FIG. 3 are conceptual diagrams showing unprocessed reception data obtained by performing phasing addition processing on respective pieces of element data.

Parts (a) to (i) of FIG. 3 show a state where a reflection point exists on a line corresponding to an n-th element.

First, an example where two or more pieces of unprocessed reception data are generated from one piece of element data will be described referring to parts (a) to (c) of FIG. 3. Part (a) of FIG. 3 is a diagram conceptually showing the transducer array 36 having a plurality of elements arranged. In part (a) of FIG. 3, the position of the element is represented using n, and reception elements are hatched. That is, part (a) of FIG. 3 shows that (n−4)th to (n+4)th elements are reception elements with the n-th element as a central element.

Part (b) of FIG. 3 is a diagram conceptually showing element data acquired by reception element shown in part (a) of FIG. 3. The position of part (b) of FIG. 3 is displayed corresponding to the position of reception element shown in part (a) of FIG. 3.

In the following description, the element data obtained using the n-th element as a central element is referred to as n-th element data.

The phasing addition unit 22 reads n-th element data from the element data storage unit 20 and performs the phasing addition processing with a line (hereinafter, referred to as an n-th line) corresponding to the n-th element as a reference line to generate n(n)-th unprocessed reception data shown at the center of part (c) of FIG. 3. The phasing addition unit 22 performs the phasing addition processing on n-th element data with an (n−2)th line as a reference line to generate n(n−2)th unprocessed reception data shown on the left of part (c) of FIG. 3. Similarly, the phasing addition processing is performed on n-th element data with (n−1)th, (n+1)th, and (n+2)th lines as a reference line to generate n(n−1)th unprocessed reception data, n(n+1)th unprocessed reception data, and n(n+2)th unprocessed reception data.

In this specification, for example, reception data generated by performing phasing addition on x-th element data with a y-th line as a reference is represented as x(y)-th reception data.

That is, the phasing addition unit 22 of this embodiment performs the phasing addition processing on one piece of element data with five lines in total including the line corresponding to the central element of the reception element corresponding to element data and the lines corresponding to the respective two elements on the right and left of the central element to generate five pieces of unprocessed reception data as shown in part (c) of FIG. 3.

Accordingly, as shown in parts (d) to (f) of FIG. 3, the phasing addition processing is performed on (n−1)th element data with (n−3)th to (n+1)th lines centering on the (n−1)th line to generate five pieces of unprocessed reception data shown in part (f) of FIG. 3. As shown in parts (g) to (i) of FIG. 3, the phasing addition processing is performed on (n+1)th element data with (n−1)th to (n+3)th lines centering on the (n+1)th line to generate five pieces of unprocessed reception data shown in part (i) of FIG. 3.

In this way, the phasing addition unit 22 performs the phasing addition processing on necessary element data multiple times while shifting an element to be a reference, and generates a plurality of pieces of unprocessed reception data.

The phasing addition unit 22 supplies unprocessed reception data to the reception data storage unit 23 and the data processing unit 24.

In the phasing addition unit 22, the number of pieces of unprocessed reception data generated from one piece of element data is not particularly limited, and may be appropriately determined according to the performance of the device, a required processing rate (frame rate or the like), image quality, and the like.

Preferably, the phasing addition unit 22 generates a larger number of pieces of unprocessed reception data than the number of pieces of unprocessed reception data to be superimposed by the data processing unit 24 described below in a measurement mode. With this, in a case of generating an ultrasound image in a cine-reproduction mode, the number of pieces of unprocessed reception data for use in superimposition is made greater than that at a real time (measurement mode), thereby improving image quality.

It is preferable that the phasing addition unit 22 generates, according to the width of the ultrasound beam, unprocessed reception data for the lines corresponding to the width.

That is, in a case of changing the number of times of superimposition in the superimposition processing in the data processing unit described below according to the width of the transmission beam of the ultrasonic beam, it is preferable that phasing addition is performed with a central element of reception elements corresponding to element data as a reference for each piece of element data according to the number of times of superimposition, and the phasing addition processing is performed for the number of times of superimposition while changing an element to be a reference of phasing addition.

For example, in a case where the number of times of superimposition is 11, the phasing addition processing is performed with five elements including a central element of reception elements corresponding to element data subjected to processing and two elements on each of the right and left of the central element as a reference.

With this, it is possible to sufficiently exhibit the effect of superimposition and to reduce the amount of data to be stored.

In a case where the number of times of superimposition in the data processing unit 24 is changed depending on the depth, the phasing addition unit 22 may generate a plurality of pieces of unprocessed reception data for one piece of element data while changing the number of times of the phasing addition processing depending on the depth, or may generate a number of pieces of unprocessed reception data corresponding to the maximum width of the ultrasound beam without depending on the depth.

Specifically, it is preferable that the phasing addition unit 22 generates unprocessed reception data for three to ten lines for one piece of element data.

The reception data storage unit 23 sequentially stores unprocessed reception data supplied from the phasing addition unit 22. The reception data storage unit 23 stores information relating to the frame rate input from the control unit 30 in association with each piece of unprocessed reception data.

The reception data storage unit 23 stores all pieces of generated reception data and does not erase unprocessed reception data until erasure of data is instructed by an input operation from the operating unit 32.

The data processing unit 24 is a unit which superimposes unprocessed reception data to generate processed reception data (second reception data) corresponding to each piece of unprocessed reception data.

Specifically, in a case where the mode selected by the mode switching unit 31 described below is a measurement mode, the data processing unit 24 superimposes unprocessed reception data obtained by performing the phasing addition processing on unprocessed reception data supplied from the phasing addition unit 22 with the same line according to the reception time of the ultrasonic echo in each ultrasound transducer to generate processed reception data.

In a case where the mode selected by the mode switching unit 31 is a cine-reproduction mode, the data processing unit 24 reads unprocessed reception data stored in the reception data storage unit 23 and superimposes unprocessed reception data subjected to the phasing addition processing with the same line according to the reception time of the ultrasonic echo in each ultrasound transducer to generate processed reception data.

The processing in the data processing unit 24 will be described below in detail.

The data processing unit 24 sends the generated processed reception data to the image generation unit 25.

The image generation unit 25 generates an ultrasound image from processed reception data (sound ray signal) supplied from the data processing unit 24 under the control of the control unit 30.

The image generation unit 25 has a detection processing unit 40, a DSC 42, an image processing unit 44, and an image memory 46.

The detection processing unit 40 performs correction of attenuation depending on the distance according to the depth of the reflection point of the ultrasonic wave on processed reception data supplied from the data processing unit 24, and then performs envelope detection processing to generate B mode image data which is tomographic image information (luminance image information) in the subject.

The digital scan converter (DSC) 42 converts (raster-converts) B mode image data generated by the detection processing unit 40 to image data corresponding to a typical television signal scan system.

The image processing unit 44 performs various kinds of necessary image processing, such as gradation processing, on B mode image data input from the DSC 42 to generates B mode image data which is used for display. The image processing unit 44 outputs B mode image data subjected to the image processing to the display control unit 26 for display and/or stores B mode image data in the image memory 46.

The image memory 46 is known storage means (storage medium) which stores B mode image data processed by the image processing unit 44. B mode image data stored in the image memory 46 is read to the display control unit 26 for display on the display unit 28 as necessary.

The display control unit 26 makes the display unit 28 display the ultrasound image using B mode image data subjected to predetermined image processing by the image processing unit 44.

The display unit 28 includes, for example, a display device, such as a liquid crystal display (LCD), and displays the ultrasound image under the control of the display control unit 26.

The mode switching unit 31 is a unit which selects (switches) an operation mode of the ultrasound diagnostic apparatus 10 based on a command input by the operator using the operating unit 32.

Specifically, the ultrasound diagnostic apparatus 10 has, as the operation mode, a measurement mode for reproducing the ultrasound image in real time based on the received ultrasonic echo while performing transmission and reception of the ultrasonic wave using the transmission unit 14 and the reception unit 16 and a cine-reproduction mode for reproducing the ultrasound image using unprocessed reception data stored in the reception data storage unit 23 without performing transmission and reception of the ultrasonic wave. The mode switching unit 31 selects the measurement mode or the cine-reproduction mode based on an input instruction from the operating unit 32 and supplies information relating to the selected mode to the control unit 30 so as to make each unit of the ultrasound diagnostic apparatus 10 perform an operation of each mode.

The control unit 30 is a unit which performs various kinds of control of the ultrasound diagnostic apparatus 10 based on a command input by the operator using the operating unit 32 and information relating to the operation mode from the mode switching unit 31.

The control unit 30 supplies various kinds of information input by the operator using the operating unit 32 to necessary units. For example, in a case where information necessary for switching the mode used in the mode switching unit 31, information necessary for calculating the delay time used in the phasing addition unit 22 and the data processing unit 24, and information necessary for processing unprocessed reception data in the data processing unit 24 are input using the operating unit 32, these kinds of information are supplied to the respective units including the transmission unit 14, the reception unit 16, the element data storage unit 20, the phasing addition unit 22, the data processing unit 24, the image generation unit 25, the display control unit 26, and the like as necessary.

The operating unit 32 is used when the operators performs an input operation, and includes a keyboard, a mouse, a trackball, a touch panel, and the like.

The operating unit 32 includes an input function of allowing the operator to input various kinds of information as necessary. For example, the operating unit 32 includes an input function of inputting information relating to the probe 12 (ultrasound transducers), the transmission opening and the reception opening in the probe 12 (transducer array 36), information relating to the generation of processed element data, such as the number of pieces of reception data to be superimposed or a superimposition method, the focal position of the ultrasound beam, and the like.

These kinds of information are input, for example, by selection of an imaging region (diagnosis region), selection of image quality, selection of the depth of an ultrasound image to be captured, and the like.

The storage unit 34 stores an operation program for allowing the control unit 30 to control the respective units of the ultrasound diagnostic apparatus 10, the transmission delay pattern and the reception delay pattern, information relating to the phasing addition processing, information relating to the generation of processed reception data, information relating to the operation mode, and information necessary for allowing the control unit 30 to operate or control the ultrasound diagnostic apparatus, such as information relating to the probe 12, the transmission opening and the reception opening, and information relating to the focal position input from the operating unit 32.

For the storage unit 34, known recording mediums, such as a hard disk, a flexible disk, a magneto-optical disk (MO), a masking tape (MT), a random access memory (RAM), a CD-ROM, and a DVD-ROM, are available.

In the ultrasound diagnostic apparatus 10, the phasing addition unit 22, the data processing unit 24, the detection processing unit 40, the DSC 42, the image processing unit 44, the display control unit 26, and the like are constituted of a CPU and an operation program which causes the CPU to perform various kinds of processing. However, in the invention, these units may be constituted using digital circuits.

Next, the data processing unit 24 will be described in detail.

As described above, the data processing unit 24 is a unit which acquires unprocessed reception data supplied from the phasing addition unit 22 or unprocessed reception data stored in the reception data storage unit 23 according to the operation mode selected by the mode switching unit 31 and superimposes two or more pieces of unprocessed reception data subjected to the phasing addition processing (reception focusing processing) with the same element (same line) as a reference according to the reception time in each ultrasound transducer to generate processed reception data.

In the measurement mode and the cine-reproduction mode, the processing in the data processing unit 24 is the same processing except that the data acquisition method is different and the number of times of superimposition is different; thus, in the following description, the processing in the cine-reproduction mode will be described, and description of the processing in the measurement mode will be provided only for the difference.

FIG. 4 conceptually shows the configuration of the data processing unit 24 using a block diagram.

As shown in FIG. 4, the data processing unit 24 has a processing condition setting unit 45, a data acquisition unit 47, a delay time calculation unit 48, and a superimposition processing unit 49.

The processing condition setting unit 45 is a unit which sets the number of pieces of unprocessed reception data to be superimposed by the superimposition processing unit 49 in the cine-reproduction mode based on a command input from the operating unit 32 or under the control of the control unit 30.

The processing condition setting unit 45 sets the number of times of superimposition in the cine-reproduction mode independently from the number of times of superimpositions in the measurement mode. Accordingly, the number of times of superimposition of unprocessed reception data in the superimposition processing unit 49 in the cine-reproduction mode can be made different from that at the real time (measurement mode), and an ultrasound image of a different image quality can be generated by changing the number of times of superimposition.

For example, the number of times of superimpositions in the cine-reproduction mode is made greater than that in the measurement mode, whereby it is possible to obtain a higher-image quality ultrasound image than that at the real time.

For example, in a case where there is a motion in a subject of a captured image, such as a heart, if the number of times of superimposition is increased, proper superimposition may not be performed and image quality may be degraded. In such a case, in the cine-reproduction mode, the number of times of superimposition is made smaller than that in the measurement mode, whereby it is possible to prevent degradation of image quality.

The processing condition setting unit 45 supplies information relating to the set number of times of superimposition to the data acquisition unit 47 and the superimposition processing unit 49.

The data acquisition unit 47 acquires unprocessed reception data to be superimposed from the phasing addition unit 22 information relating to the number of times of superimposition set in advance in the measurement mode. In the cine-reproduction mode, unprocessed reception data to be superimposed is read from the reception data storage unit 23 based on information relating to the number of times of superimposition supplied from the processing condition setting unit 45.

The data acquisition unit 47 supplies the acquired unprocessed reception data to the superimposition processing unit 49.

The delay time calculation unit 48 acquires information relating to the probe 12 (ultrasound transducers (elements)), the focal position of the ultrasound beam, a position of a sampling point (an output position of element data), the transmission opening and the reception opening of the probe 12, and the like input from the operating unit 32 or input from the operating unit 32 and stored in the storage unit 34 in advance.

The delay time calculation unit 48 calculates a delay time of an ultrasonic echo received by the element of the reception opening, that is, unprocessed reception data based on the geometrical positions of the element of the transmission opening which oscillates an ultrasonic wave to transmit (generate) an ultrasound beam and the element of the reception opening which receives an ultrasonic echo from the subject.

The delay time calculation unit 48 supplies information relating to the calculated delay time to the superimposition processing unit 49.

The superimposition processing unit 49 superimposes two or more pieces of unprocessed reception data according to the time based on information relating to the number of times of superimposition set by the processing condition setting unit 45, information relating to the processing on element data, such as the superimposition processing method, input from the operating unit 32 or input from the operating unit 32 and stored in the storage unit 34, and the delay time corresponding to each piece of unprocessed reception data calculated by the delay time calculation unit 48 to generate processed reception data.

Hereinafter, the processing on unprocessed reception data which is performed by the data processing unit 24 will be described in detail.

First, in the ultrasound probe 12, in a case where an ultrasound beam is transmitted from a transmission opening, that is, an element (hereinafter, simply referred to as a transmission element), which oscillates an ultrasonic wave to transmit an ultrasound beam, to a subject, and an ultrasonic echo generated by an interaction with the subject is received by a reception opening, that is, an element (hereinafter, simply referred to as a reception element) which receives an ultrasonic echo to obtain element data, the relationship between the ultrasound beam from the transmission element and element data obtained by the reception element will be described.

As an example, as shown in FIG. 5A, an ultrasound beam is transmitted with three elements 52c to 52e as a transmission element, and an ultrasonic echo is received with seven elements 52a to 52g as a reception element. Next, as shown in FIG. 5C, the elements are moved (hereinafter, also referred to as shifted) in the azimuth direction for one element, an ultrasound beam is transmitted with three elements 52d to 52f as a transmission element, and an ultrasonic echo is received with seven elements 52b to 52h as a reception element to acquire element data.

That is, in the example shown in FIG. 5A, a central element (an element to be the center) is the element 52d, and in the example shown in FIG. 5C, a central element is the element 52e.

At this time, an ideal case where an ultrasound beam 56 which is transmitted to a region to be inspected including a reflection point 54 is converged on a focal point 58 and is narrowed to an element interval or less is considered.

As in FIG. 5A, the element 52d directly above the reflection point 54 (on a straight line connecting the reflection point and the focal point) is used as a central element, the ultrasound beam 56 is transmitted from the elements 52c to 52e as a transmission element, and the ultrasonic echo is received by the elements 52a to 52g as a reception element to acquire element data, the focal point 58 of the ultrasound beam 56 is on a straight line connecting the element 52d as a central element and the reflection point 54. In this case, since the ultrasound beam 56 is transmitted to the reflection point 54, the ultrasonic echo reflected from the reflection point 54 is generated.

The ultrasonic echo from the reflection point 54 is received by the elements 52a to 52g as a reception element through a reception path 60 which expands at a predetermined angle, and element data 62 shown in FIG. 5B is obtained by the elements 52a to 52g. In FIG. 5B, the vertical axis is time, and the horizontal axis is the position (the position of the element) in the azimuth direction corresponding to FIG. 5A (the same applies to FIG. 5D).

In contrast, as shown in FIG. 5C, in a case where the central element is shifted for one element, the element 52e adjacent to the element 52d directly above the reflection point 54 becomes a central element.

The element 52e is used as a central element, the ultrasound beam 56 is transmitted from the elements 52d to 52f as a transmission element, and the ultrasonic echo is received by the elements 52b to 52h as a reception element. At this time, similarly, if the ultrasound beam 56 is ideal, the reflection point 54 does not exist in the transmission direction of the ultrasound beam 56, that is, on a straight line connecting the central element 52e and the focal point 58. Accordingly, the ultrasound beam 56 is not transmitted to the reflection point 54.

For this reason, the ultrasonic echo reflected from the reflection point 54 is not generated, and the elements 52b to 52h as a reception element do not receive the ultrasonic echo from the reflection point 54; thus, as shown in FIG. 5D, element data including no reflection signal from the reflection point is obtained (the signal strength of element data becomes "0").

However, since an actual ultrasound beam is converged on the focal point 58 and then diffused like an ultrasound beam 64 shown in FIGS. 6A and 6C, the width is larger than the element interval.

Similarly to FIG. 5A, as in FIG. 6A, in a case where the element 52d directly above the reflection point 54 is used as a central element, and an ultrasound beam 64 is transmitted with the elements 52c to 52e as a transmission element, even if the ultrasound beam 56 has a large width, the focal point 58 is on a straight line connecting the element 52d and the reflection point 54. Accordingly, the ultrasound beam 64 is reflected from the reflection point 54, and the ultrasonic echo is generated.

As a result, similarly to the case of FIG. 5A, the ultrasonic echo from the reflection point 54 is received by the elements 52*a* to 52*g* as a reception element through a reception path 60 which expands at a predetermined angle, and similarly, element data 66 (hereinafter, for convenience, referred to as "true element data") including a true signal shown in FIG. 6B is obtained.

Next, similarly to FIG. 5C, as shown in FIG. 6C, the central element is shifted for one element, the adjacent element 52*e* is used as a central element, the ultrasound beam 56 is transmitted with the elements 52*d* to 52*f* as a transmission element, and the ultrasonic echo is received with the elements 52*b* to 52*h* as a reception element. In this case, since the ultrasound beam 64 has a large width, even if the reflection point 54 does not exist in the transmission direction of the ultrasonic wave, that is, on a straight line connecting the element 52*e* as a central element and the focal point 58, the ultrasound beam 64 is transmitted to (reaches) the reflection point 54.

For this reason, an ultrasonic echo, so-called a reflection echo of ghost, which does not originally exist, is generated from the reflection point 54 in the transmission direction of the ultrasound beam. As shown in FIG. 6C, the reflection echo of ghost from the reflection point 54 is received by the elements 52*b* to 52*h* as a reception element through the reception path 60 which expands at a predetermined angle. As a result, element data 68 (hereinafter, for convenience, referred to as "element data of ghost") including a ghost signal shown in FIG. 6D is obtained by the elements 52*b* to 52*h*.

Such element data 68 of ghost causes degradation of the accuracy of an ultrasound image generated from element data.

In contrast, in the processing in the data processing unit 24, the delay time corresponding to unprocessed reception data is calculated and two or more pieces of unprocessed reception data are superimposed according to the delay time, whereby processed reception data which is high-accuracy reception data with a true signal enhanced and a ghost signal attenuated is generated.

The calculation method of the delay time in the delay time calculation unit 48 will be described below in detail.

That is, the propagation distance of the ultrasound beam 64 shown in FIG. 6C is the sum of a transmission path along which the ultrasound beam 64 reaches the reflection point 54 from the element 52*e* as a central element through the focal point 58 and a reception path along which the reflection echo of ghost reaches each of the elements 52*b* to 52*h* as a reception element from the reflection point 54.

The propagation distance of the ultrasound beam 64 shown in FIG. 6C becomes longer than the propagation distance of the ultrasound beam 64 shown in FIG. 6A, that is, the sum of a transmission path along which the ultrasound beam 64 reaches the reflection point 54 from the central element 52*d* through the focal point 58 and a reception path along which a true ultrasonic echo reaches the elements 52*a* to 52*g* as a reception element from the reflection point 54.

For this reason, element data 68 of ghost shown in FIG. 6D is delayed with respect to true element data 66 shown in FIG. 6B.

In the delay time calculation unit 48, the time difference between the true signal and the ghost signal, that is, the delay time, is calculated from a sound speed, the transmission elements, the focal point of the ultrasound beam, the reflection point of the subject, and the geometrical arrangement of the reception elements.

Accordingly, the calculation of the delay time requires information relating to the shape (element interval, linear shape, convex shape, or the like) of the probe 12, the sound speed, the position of the focal point, the transmission opening, the reception opening, and the like. In the delay time calculation unit 48, these kinds of information input from the operating unit 32 or stored in the storage unit 34 are acquired to perform the calculation of the delay time. For the sound speed, a fixed value (for example, 1540 m/sec) may be used, in a case where a sound speed calculation unit is provided, a sound speed (environmental sound speed) calculated by the sound speed calculation unit may be used, or a sound speed may be input by the operator.

The delay time can be calculated from the difference between the total length (propagation distance) of the transmission path of the ultrasound beam reaching the reflection point from the transmission element through the focal point and the reception path of the true reflection ultrasonic echo or the reflection signal of ghost reaching the reception element from the reflection point calculated from the transmission elements, the focal point of the ultrasound beam, the reflection point of the subject, and the geometrical arrangement of the reception elements, and a propagation time calculated by the sound speed.

In the invention, for example, as shown in FIGS. 7A and 7B, it is possible to determine the length of the transmission path and the reception path of the ultrasound beam in cases of the true ultrasonic echo and the reflection echo of ghost. In FIGS. 7A and 7B, the x direction is an azimuth direction, and the y direction is a depth direction.

FIG. 7A shows the same transmission and reception of an ultrasonic wave as in FIG. 6A, and FIG. 7B shows the same transmission and reception of an ultrasonic wave as in FIG. 6C.

In a case of the true ultrasonic echo, as shown in FIG. 7A (FIG. 6A), the element 52*d* as a central element, the focal point 58, and the reflection point 54 are positioned on a straight line (the positions in the azimuth direction match one another). That is, the focal point 58 and the reflection point 54 are positioned directly below the central element 52*d*.

Accordingly, if the position of the element 52*d* as a central element is set to the coordinates (x0,0) on two-dimensional coordinates of x-y, the x coordinates of the focal point 58 and the reflection point 54 become "x0". Hereinafter, the position of the focal point 58 in the transmission is set to the coordinates (x0,df), the position of the reflection point 54 is set to the coordinates (x0,z), and the element interval is referred to as Le.

At this time, the length (transmission path distance) Lta of a transmission path 61 of the ultrasound beam reaching the reflection point 54 from the element 52*d* as a central element through the focal point 58 and the length (reception path distance) Lra of a reception path 60 of the true reflection ultrasonic echo reaching the element 52*d* from the reflection point 54 can be calculated by Lta=Lra=z.

Accordingly, in a case of the true ultrasonic echo, a propagation distance Lua of the ultrasonic echo becomes Lua=Lta+Lra=2z.

Next, as shown in FIG. 7B, the transmission elements and the reception elements are shifted for one element in the x direction (azimuth direction) (shifted in the right direction of the drawing), and transmission and reception are performed with the element 52e as a central element. As shown in FIG. 6C, in this case, the reflection echo of ghost is reflected from the reflection point 54.

The reflection point 54 is positioned directly below the element 52d (the same position in the azimuth direction). Accordingly, as shown in FIG. 7B, in the transmission and reception, the positions of the element 52e as a central element and the reflection point 54 in the x direction are shifted in the x direction for one element, that is, by Le.

Since the coordinates of the element 52d whose position in the x direction matches the reflection point 54 are (x0,0), the coordinates of the element 52e as a central element become (x0+Le,0), and the coordinates of the focal point 58 in the transmission become (x0+Le,df). As described above, the coordinates of the reflection point 54 are (x0,z).

Accordingly, the length (transmission path distance) Ltb of the transmission path 61 of the ultrasound beam reaching the reflection point 54 from the element 52e as a central element through the focal point 58 can be calculated by $Ltb = df + \sqrt{(z-df)^2 + Le^2}$. The length (reception path distance) Lrb of the reception path 60 of the reflection signal of ghost reaching the element 52d directly below the reflection point 54 (the same position in the x direction=the azimuth direction) from the reflection point 54 can be calculated by $Lrb = z$.

Accordingly, in a case of the reflection echo of ghost, the propagation distance Lub of the ultrasonic wave becomes $Lub = Ltb + Lrb = df + \sqrt{(z-df)^2 + Le^2} + z$.

In this way, a value obtained by dividing the propagation distance Lua of the ultrasonic wave as the sum of the distance Lta of the transmission path 61 and the distance Lra of the reception path 60 determined from the geometrical arrangement shown in FIG. 7A by the sound speed becomes the propagation time of the true ultrasonic echo. A value obtained by dividing the propagation distance Lub of the ultrasonic wave as the sum of the distance Ltb of the transmission path 61 and the distance Lrb of the reception path 60 determined from the geometrical arrangement shown in FIG. 7B by the sound speed becomes the propagation time of the reflection echo of ghost.

The delay time is determined from the difference between the propagation time of the true ultrasonic echo when the x coordinates of the reflection point 54 and the central element match each other and the propagation time of the reflection echo of ghost when the x coordinates of the reflection point 54 and the central element are shifted by one element interval.

In the geometrical models of FIGS. 7A and 7B, although a model in which the transmission path 61 passes through the focal point 58 has been shown, the invention is not limited thereto, and for example, the transmission path may be a path which directly reaches the reflection point 54 without passing through the focal point 58.

Although the geometrical models of FIGS. 7A and 7B are applied to a linear probe, the invention is not limited thereto, in other probes, the same geometrical calculation can be performed from the shape of the probe.

For example, in a case of a convex probe, a geometrical model can be set from the radius of the probe and the angle of the element interval, and the same calculation can be performed.

In a case of steering transmission, a geometrical model in consideration of information relating to a transmission angle and the like can be used, and the delay time can be calculated from the positional relationship between the transmission element and the reflection point.

The invention is not limited to the calculation method of the delay time using the geometrical model, and a delay time may be determined for each measurement condition from a measurement result of measuring a high-luminance reflection point according to the measurement conditions of the device in advance, the delay time may be stored in the device, and the delay time of the same measurement condition may be read.

FIG. 7C shows true element data 66 and element data 68 of ghost.

In FIG. 7C, the center in the azimuth direction is true element data 66, that is, element data (in the example of the drawing, element data with the element 52d as a central element) obtained by transmission and reception in which the positions of the central element and the reflection point 54 in the x direction match each other. Both sides of the center are element data of ghost, that is, element data (in the example of the drawing, element data with the element 52c, the element 52e, or the like as a central element) obtained by transmission and reception in which the positions of the central element and the reflection point 54 in the x direction do not match each other.

FIG. 7D shows an example of the delay time of element data 68 with respect to true element data 66 obtained from the above-described geometrical calculation. True element data 66 is at the center, and element data 68 of the ghost signal is delayed symmetrically in the x direction, that is, in the azimuth direction.

In this way, the delay time calculated in the delay time calculation unit 48 of the data processing unit 24 may be used for delay correction in the phasing addition unit 22.

Though described below in detail, in the invention, unprocessed reception data obtained by performing the phasing addition processing on element data obtained by transmission of the ultrasound beam with a certain element of interest as a central element (transmission and reception of the element of interest) with a line corresponding to the element of interest (central element) as a reference and unprocessed reception data obtained by performing the phasing addition processing on element data obtained by transmission and reception of the ultrasonic wave with a different central element with the line corresponding to the element of interest as a reference are superimposed based on the delay time with the element of interest as a reference to generate processed reception data (second reception data) of the element of interest.

In FIG. 7A, the reflection point 54 indicates the position (the output position of element data) of a certain sampling point directly below the element of interest (on the same position in the azimuth direction/a straight line connecting the element of interest and the focal point). In the invention, the transmission and reception path to the sampling point in the transmission and reception of the element of interest is regarded as the transmission and reception path of true element data, the transmission and reception path to the same sampling point in transmission and reception of an ultrasonic wave with a different central element (transmission and reception from a peripheral element) is regarded as the transmission and reception path of ghost, the delay time is calculated from the difference between both transmission paths, and superimposition is performed using the delay time according to the time of unprocessed reception data.

In the invention, the delay time is calculated by the same way of thinking corresponding to all sampling points (all output positions of element data), and superimposition of unprocessed reception data is performed to generate processed reception data of the respective elements.

Actually, even if the position of the sampling point (reflection point) is shifted in the azimuth direction (x direction), the length (reception path distance Lrb) of the reception path is not changed. Accordingly, in regard to each element of interest, the calculation of the delay time from unprocessed reception data by transmission and reception with a different central element may be performed for each sampling point in the depth direction (y direction).

In the superimposition processing, it is not necessary to know whether or not a signal is a true signal. That is, it is not necessary to know the position of the reflection point.

Though described below in detail referring to parts (a) to (h) of FIG. 8, in the superimposition processing, if a signal included in unprocessed reception data is a true signal, the signal is automatically enhanced and remains, and if a signal included in unprocessed reception data is a ghost signal, the signal is canceled. That is, if the reflection point exists on the line of the element of interest, a signal from the reflection point is enhanced by matching the processing depending on the delay time, and a signal from a reflection point on a line other than the element of interest is canceled without matching the processing depending on the delay time.

Next, in the superimposition processing unit 49 of the data processing unit 24 of the invention, the superimposition processing of unprocessed reception data is performed using the delay time calculated in the delay time calculation unit 48 in this way.

In the superimposition processing in the superimposition processing unit 49, information relating to the number of pieces of element data to be superimposed and the superimposition method at the time of superimposition is required. The number of times of superimposition in the measurement mode may be input by the operating unit 32 or stored in the storage unit 34 in advance. The number of times of superimposition in the cine-reproduction mode is set by the processing condition setting unit 45.

Hereinafter, the processing which is performed by the data processing unit 24 will be described in detail referring to parts (a) to (h) of FIG. 8.

Parts (a) and (e) of FIG. 8 are conceptual diagrams showing unprocessed reception data to be superimposed, parts (b) and (f) of FIG. 8 are conceptual diagrams illustrating the delay time of each piece of unprocessed reception data, parts (c) and (g) of FIG. 8 are conceptual diagrams illustrating a state of superimposition of unprocessed reception data, and parts (d) and (h) of FIG. 8 are conceptual diagrams illustrating a result of superimposition of unprocessed reception data.

An example shown in parts (a) to (h) of FIG. 8 is an example where the number of times of superimposition in the superimposition processing unit 49 is five.

Unprocessed reception data shown in parts (a) and (e) of FIG. 8 are conceptual diagrams of unprocessed reception data in a state where a reflection point exists on an n-th line.

As shown in part (a) of FIG. 8, in a case of generating processed reception data corresponding to n(n)th unprocessed reception data, the data acquisition unit 47 acquires five pieces of unprocessed reception data (n−2(n)th, n−1(n)th, n(n)th, n+1(n)th, and n+2(n)th unprocessed reception data) which are unprocessed reception data generated by performing the phasing addition processing on different pieces of element data with the n-th line as a reference, and supplies the five pieces of unprocessed reception data to the superimposition processing unit 49.

The superimposition processing unit 49 performs the delay time correction on the five pieces of unprocessed reception data based on the delay time (part (b) of FIG. 8) calculated by the delay time calculation unit 48, superimposes unprocessed reception data (part (c) of FIG. 8), and performs addition or averaging to generate processed reception data corresponding to n(n)th unprocessed reception data (part (d) of FIG. 8). The generated processed reception data is processed reception data corresponding to the n-th element (line).

Similarly, in a case of generating processed reception data corresponding to the (n−1)th line, the data acquisition unit 47 acquires five pieces of unprocessed reception data (part (e) of FIG. 8) generated by performing the phasing addition processing with the (n−1)th line as a reference, and supplies the five pieces of unprocessed reception data to the superimposition processing unit 49.

The superimposition processing unit 49 performs the delay time correction on the five pieces of unprocessed reception data based on the delay time (part (f) of FIG. 8), superimposes unprocessed reception data (part (g) of FIG. 8), and performs addition or averaging to generate (n−1)th processed reception data (part (h) of FIG. 8).

As in parts (a) to (d) of FIG. 8, if the delay time correction is performed on unprocessed element data subjected to the phasing addition processing with a line (n-th line) having the reflection point as a reference and superimposition is performed, the phases of the signals from the reflection point match each other; thus, the signals (true signals) from the reflection point indicate an enhanced value (high-luminance value) through the superimposition processing (part (d) of FIG. 8).

As in parts (e) to (h) of FIG. 8, even if the delay time correction is performed on unprocessed element data subjected to the phasing addition processing with a line ((n−1)th line) having no reflection point as a reference, the phases of the signals (ghost signals) from the reflection point do not match each other; thus, the signals are canceled each other and have a small value through superimposition (part (h) of FIG. 8).

In regards to other elements (lines), each element is used as an element of interest, and two or more pieces of unprocessed reception data subjected to the phasing addition processing with the line of the element of interest as a reference are read, and the superimposition processing is performed based on the delay time, whereby the true signals are enhanced and the ghost signals are canceled to reduce the influence of the ghost signals.

For this reason, since it is possible to generate the ultrasound image with reception data such that the influence of ghost is eliminated, that is, the focal points at all points on the sound ray are connected by performing detection processing or the like on processed reception data and generating the ultrasound image, it is possible to generate a high-image quality ultrasound image with high luminance and excellent sharpness.

In the following description, the processing for superimposing data obtained by receiving the ultrasonic echo based on the delay time or the position of the element to generate data with the influence of the ghost signal reduced is also referred to as multiline processing.

That is, such multiline processing may be performed using element data which is data before the phasing addition processing is performed.

However, as described above, in a device which performs multiline processing on element data to generate an ultrasound image, when the ultrasound image is reproduced in the cine-reproduction mode, in order to obtain an image of a different image quality from a real-time ultrasound image, element data needs to be stored. However, since element data has enormous volume, there is a problem in that it is difficult to store element data for many frames for cine-reproduction.

In a case of performing the multiline processing on element data to generate an ultrasound image, it is necessary to perform the multiline processing multiple times. For this reason, there is a problem in that a calculation time is increased, and a long time is required for reproduction.

In contrast, in the invention, in the measurement mode, the phasing addition processing is performed multiple times on element data acquired by performing transmission and reception of the ultrasonic wave while shifting an element to be a reference to generate a plurality of pieces of unprocessed reception data, two or more pieces of unprocessed reception data are superimposed according to the delay time to generate processed reception data, and an ultrasound image is created from processed reception data. At this time, the reception data storage unit 23 stores the generated unprocessed reception data.

Thereafter, in a case where the cine-reproduction mode is selected, the data processing unit 24 generates processed reception data using unprocessed reception data stored in the reception data storage unit 23 to create an ultrasound image.

In this way, in order to regenerate an ultrasound image in the cine-reproduction mode with a different image quality from a real time ultrasound image, unprocessed reception data generated in the measurement mode is stored. Accordingly, it is possible to reduce the amount of data to be stored for cine-reproduction, and to reduce a calculation time at the time of cine-reproduction.

In the invention, the central element is an element at the center in the azimuth direction in a case where the number of transmission openings (the number of elements which perform transmission of an ultrasonic wave) is an odd number.

Meanwhile, in a case where the number of openings is an even number, any one of the elements at the center in the azimuth direction is used as the central element, or assuming that there is an element in the middle of the azimuth direction, the element is used as the central element. That is, in a case where the number of openings is an even number, the calculation may be performed by providing a focal point on a line in the middle of the opening.

As the superimposition processing method in the superimposition processing unit 49, an average value or a median value may be taken instead of only adding, or addition may be performed after multiplication with a coefficient (applying weighting). Taking the average value or the median value may be considered equivalent to applying an averaging filter or a median filter at a reception data level; however, an inverse filter or the like which performs normal image processing may be applied instead of the averaging filter or the median filter.

Alternatively, the pieces of unprocessed reception data to be superimposed are compared, a maximum value is taken in a case where the pieces of element data are not similar, an average value is taken in a case where the pieces of element data are similar, and an intermediate value is taken in a case where th distribution is biased; however, the invention is not limited thereto, and the superimposition processing may be changed based on the feature amount of each piece of element data to be superimposed.

The number of pieces of unprocessed reception data to be superimposed on unprocessed reception data of the element of interest is not limited to four in the example of the drawing, and may be one to three, or five or more. That is, the number of pieces of element data to be superimposed on element data of the element of interest may be appropriately set according to a required processing rate (frame rate or the like), image quality, or the like.

It is preferable that the number of pieces of element data to be superimposed on element data of the element of interest matches the extent of the spread of the beam width of the ultrasound beam. Accordingly, in a case where the beam width changes according to the depth, the number of pieces of element data to be superimposed may be changed according to the depth.

Since the beam width depends on the number of transmission openings, the number of pieces of element data to be superimposed may be changed according to the number of transmission openings. Alternatively, the number of pieces of element data to be superimposed may be changed based on the feature amount, such as the luminance value of the image, or the optimum number of pieces of element data to be superimposed may be selected from an image created by changing the number of pieces of superimposed element data into a plurality of patterns.

Processed reception data generated by superimposition does not need to correspond to any of unprocessed reception data used in superimposition. That is, the generated processed reception data is data corresponding to a different position (line) from unprocessed reception data.

For example, processed reception data corresponding to a line at an intermediate position of a line corresponding to each piece of unprocessed reception data may be generated.

The number of lines for generating processed reception data may be the same as or may be greater or less than the number of lines where element data is acquired (the number of lines where transmission and reception of the ultrasonic wave are performed).

That is, for example, processed reception data corresponding to lines where element data is acquired and lines at intermediate positions of the lines may be generated, thereby generating processed reception data corresponding to the number of lines two times the number of lines where transmission and reception of the ultrasonic wave are performed.

In the above multiline processing, although processed element data of element data of the element of interest is generated by generating unprocessed reception data from element data obtained by transmission of a plurality of ultrasound beams, for which the central elements are different and the transmission directions of the ultrasound beams are parallel (the angles are the same), and superimposing unprocessed reception data, the invention is not limited thereto.

For example, processed element data may be generated by generating unprocessed reception data from element data obtained by transmission of a plurality of ultrasound beams, for which the central elements are the same and the transmission directions (angles) are different, and superimposing unprocessed reception data. At this time, whether to generate processed element data of a sound ray in any direction may be set by default according to a diagnosis region, the type of probe, or the like, or may be selected by the operator.

Processed element data may be generated using both of element data obtained by transmission where the central elements are different and the ultrasound beams are parallel and element data obtained by transmission where the central elements are the same and the transmission directions of the ultrasound beams are different.

As described above, the data processing unit 24 sends the generated processed element data to the image generation unit 25.

In the image generation unit 25 to which processed element data is supplied, as described above, the detection processing unit 40 performs attenuation correction and envelope detection processing on processed reception data to generate B mode image data.

In addition, in the image generation unit 25, the DSC 42 raster-converts B mode image data to image data corresponding to a typical television scan system, and predetermined processing, such as gradation processing, is performed in the image processing unit 44.

The image processing unit 44 stores the generated B mode image data in the image memory 46 and/or sends the generated B mode image data to the display control unit 26 and displays the B mode image of the subject on the display unit 28.

Hereinafter, a signal processing method (a signal processing method of the invention) in the ultrasound diagnostic apparatus 10 will be described in detail referring to the flowcharts shown in FIGS. 9A and 9B.

A program of the invention is a program which causes a computer in the ultrasound diagnostic apparatus 10 to execute the following signal processing method.

As shown in FIG. 9A, in the ultrasound diagnostic apparatus 10, in a case where the measurement mode is selected, first, the transmission unit 14 transmit the ultrasound beam to the subject by driving (with a predetermined number of openings and the positions of the openings) the corresponding ultrasound transducers (elements) of the probe 12 (transducer array 36) in response to an instruction from the control unit 30, the ultrasonic echoes reflected from the subject is received by the ultrasound transducers (elements), and analog reception signals are output to the reception unit 16.

The reception unit 16 performs predetermined processing, such as amplification, on the analog reception signals, and supplies the analog reception signals to the A/D conversion unit 18.

The A/D conversion unit 18 A/D converts the analog reception signals supplied from the reception unit 16 to element data as digital reception signals.

Element data is stored in the element data storage unit 20.

The phasing addition unit 22 sequentially read element data stored in the element data storage unit 20 and performs the phasing addition processing in a plurality of lines for each piece of element data.

Specifically, as shown in Parts (a) to (i) of FIG. 3, for example, the phasing addition processing is performed in the lines corresponding to the five elements in total including the central elements and both adjacent two elements to generate five pieces of unprocessed reception data for each piece of element data.

The generated unprocessed reception data is supplied to the data processing unit 24 and is stored in the reception data storage unit 23.

The data processing unit 24 performs the superimposition processing of the supplied unprocessed reception data to generate processed reception data.

Specifically, as shown in parts (a) to (h) of FIG. 8 described above, for example, the data processing unit 24 performs the delay time correction on unprocessed reception data generated by performing phasing addition on element data of the element of interest in the line of the element of interest and unprocessed reception data generated by performing phasing addition on both adjacent two pieces of element data of the element of interest in the line of the element of interest with respect to the element of interest and superimposes unprocessed reception data to generate processed reception data of the element of interest.

The image generation unit 25 generates an ultrasound image (B mode image data) using processed reception data corresponding to a predetermined number of a plurality of elements generated by the data processing unit 24.

As shown in FIG. 9B, after the measurement, if the cine-reproduction mode is selected, the data processing unit 24 reads unprocessed reception data stored in the reception data storage unit 23 according to the number of times of superimposition set by the processing condition setting unit 45.

The superimposition processing unit 49 of the data processing unit 24 performs the superimposition processing on the read unprocessed reception data to generate processed reception data.

The image generation unit 25 generates an ultrasound image (B mode image data) using processed reception data corresponding to a predetermined number of a plurality of elements generated by the data processing unit 24.

Although the acoustic wave processing device, the signal processing method, and the program of the invention have been described in detail, the invention is not limited to the above-described example, and various improvements or alterations may be of course made without departing from the spirit of the invention.

EXPLANATION OF REFERENCES

10: ultrasound diagnostic apparatus
12: (ultrasound) probe
14: transmission unit
16: reception unit
18: A/D conversion unit
20: element data storage unit
22: phasing addition unit
23: reception data storage unit
24: data processing unit
25: image generation unit
26: display control unit
28: display unit
30: control unit
32: operating unit
34: storage unit
36: transducer array
40: detection processing unit
42: DSC
44: image processing unit
46: image memory
47: data acquisition unit
48: delay time calculation unit
49: superimposition processing unit
52: element
54: reflection point
56, 64: ultrasound beam
58: focal point
60: reception path
61: transmission path
62: element data
66: true element data
68: element data of ghost

What is claimed is:

1. An acoustic wave processing device comprising:
 a probe which has a plurality of elements arranged to transmit an acoustic beam, to receive an acoustic echo reflected from an object to be inspected, and to output an analog element signal according to the received acoustic echo;
 a processor; and a memory,
wherein the processor is configured to:
use two or more elements among the plurality of elements as a transmission element and make the probe transmit the acoustic beam multiple times so as to form a predetermined transmission focal point;
receive an acoustic echo corresponding to each transmission of the acoustic beam with two or more elements among the plurality of elements as a reception element, receives analog element signals output from the reception elements, and perform predetermined processing on the analog element signals;
perform A/D conversion on the analog element signals to convert the analog element signals to first element data as a digital element signal; and
perform phasing addition on the respective pieces of first element data with at least two elements as a reference to generate at least two pieces of first reception data for each piece of first element data,
wherein the memory stores a plurality of pieces of first reception data, and
the processor is further configured to:
read two or more pieces of first reception data from the plurality of pieces of first reception data stored in the memory;
superimpose the two or more pieces of first reception data to generate second reception data;
set the number of pieces of first reception data for use when generating the second reception data;
switch between a measurement mode for performing transmission and reception of the acoustic wave and reproducing an image based on the received acoustic echo and a cine-reproduction mode for generating and reproducing an image using the plurality of pieces of first reception data stored in the memory without performing transmission and reception of the acoustic wave; and
in the cine-reproduction mode, read the first reception data, the number of pieces of which is set, from the memory, and superimpose the read first reception data to generate the second reception data.

2. The acoustic wave processing device according to claim 1,
wherein the processor is further configured to read the two or more pieces of first reception data generated from different pieces of first element data and generated through phasing addition with the same element as a reference from the plurality of pieces of first reception data stored in the memory.

3. The acoustic wave processing device according to claim 1,
wherein the processor is further configured to superimpose the two or more pieces of first reception data according to a reception time of an acoustic echo received by each element to generate the second reception data.

4. The acoustic wave processing device according to claim 2,
wherein the processor is further configured to superimpose the two or more pieces of first reception data according to a reception time of an acoustic echo received by each element to generate the second reception data.

5. The acoustic wave processing device according to claim 1,
wherein the processor is further configured to superimpose two or more pieces of first reception data to generate the second reception data in the measurement mode, and
the number of times of phasing addition which is performed on one piece of first reception data is greater than the number of times of superimposition in the measurement mode.

6. The acoustic wave processing device according to claim 2,
wherein the processor is further configured to superimpose two or more pieces of first reception data to generate the second reception data in the measurement mode, and
the number of times of phasing addition which is performed on one piece of first reception data is greater than the number of times of superimposition in the measurement mode.

7. The acoustic wave processing device according to claim 3,
wherein the processor is further configured to superimpose two or more pieces of first reception data to generate the second reception data in the measurement mode, and
the number of times of phasing addition which is performed on one piece of first reception data is greater than the number of times of superimposition in the measurement mode.

8. The acoustic wave processing device according to claim 4,
wherein the processor is further configured to superimpose two or more pieces of first reception data to generate the second reception data in the measurement mode, and
the number of times of phasing addition which is performed on one piece of first reception data is greater than the number of times of superimposition in the measurement mode.

9. The acoustic wave processing device according to claim 1,
wherein the processor is further configured to superimpose two or more pieces of first reception data to generate the second reception data in the measurement mode, and
the number of times of superimposition of the first reception data in the cine-reproduction mode is greater than the number of times of superimposition in the measurement mode.

10. The acoustic wave processing device according to claim 2,
wherein the processor is further configured to superimpose two or more pieces of first reception data to generate the second reception data in the measurement mode, and
the number of times of superimposition of the first reception data in the cine-reproduction mode is greater than the number of times of superimposition in the measurement mode.

11. The acoustic wave processing device according to claim 3,
wherein the processor is further configured to superimpose two or more pieces of first reception data to generate the second reception data in the measurement mode, and the number of times of superimposition of the first reception data in the cine-reproduction mode is greater than the number of times of superimposition in the measurement mode.

12. The acoustic wave processing device according to claim 4,
wherein the processor is further configured to superimpose two or more pieces of first reception data to generate the second reception data in the measurement mode, and
the number of times of superimposition of the first reception data in the cine-reproduction mode is greater than the number of times of superimposition in the measurement mode.

13. The acoustic wave processing device according to claim 5,
wherein the processor is further configured to superimpose two or more pieces of first reception data to generate the second reception data in the measurement mode, and
the number of times of superimposition of the first reception data in the cine-reproduction mode is greater than the number of times of superimposition in the measurement mode.

14. The acoustic wave processing device according to claim 6,
wherein the processor is further configured to superimpose two or more pieces of first reception data to generate the second reception data in the measurement mode, and
the number of times of superimposition of the first reception data in the cine-reproduction mode is greater than the number of times of superimposition in the measurement mode.

15. The acoustic wave processing device according to claim 1,
wherein the number of times of phasing addition which is performed on one piece of first reception data is set according to the width of the acoustic beam.

16. The acoustic wave processing device according to claim 1,
wherein the processor is further configured to perform at least one of change of a central element or change of a transmission direction of an acoustic beam to make the probe transmit the acoustic beam multiple times.

17. The acoustic wave processing device according to claim 1,
wherein the processor is further configured to apply weighting to the two or more pieces of first reception data and superimposes the two or more pieces of first reception data to generate the second reception data.

18. The acoustic wave processing device according to claim 1, wherein the processor is further configured to receive an input instruction for setting the number of times of superimposition, and
wherein the processor is further configured to superimpose the first reception data based on the input instruction to generate the second reception data.

19. A signal processing method for the acoustic wave processing device according to claim 1, which inspects an object to be inspected using a probe having a plurality of elements arranged to transmit an acoustic beam, to receive an acoustic echo reflected from the object to be inspected, and to output an analog element signal according to the received acoustic echo, the signal processing method comprising:

a transmission step of using two or more elements among the plurality of elements of the probe as a transmission element and making the probe transmit the acoustic beam multiple times so as to form a predetermined transmission focal point;
a reception time of receiving an acoustic echo corresponding to each transmission of the acoustic beam with two or more elements among the plurality of elements as a reception element and outputting an analog element signal;
an A/D conversion step of performing A/D conversion on the analog element signal to generate first element data as a digital element signal;
a phasing addition step of performing phasing addition on the respective pieces of generated first element data with at least two elements as a reference to generate at least two pieces of first reception data for each piece of first element data;
a reception data storage step of storing a plurality of pieces of first reception data generated in the phasing addition step;
a data acquisition step of reading two or more pieces of first reception data from the plurality of pieces of first reception data stored in the reception data storage step;
a reception data generation step of superimposing the two or more pieces of first reception data read in the data acquisition step to generate second reception data;
a processing condition setting step of setting the number of pieces of first reception data for use when generating the second reception data in the reception data generation step; and
a mode switching step of switching between a measurement mode for performing transmission and reception of the acoustic wave and reproducing an image based on the received acoustic echo and a cine-reproduction mode for generating and reproducing an image using the plurality of pieces of first reception data stored in the memory without performing transmission and reception of the acoustic wave,
wherein, in the cine-reproduction mode, the first reception data, the number of pieces of which is set in the processing condition setting step, is read from the memory in the data acquisition step, and the read first reception data is superimposed to generate the second reception data in the reception data generation step.

20. A non-transitory computer readable recording medium storing a program which causes a computer to execute a signal processing method for the acoustic wave processing device according to claim 1, which inspects an object to be inspected using a probe having a plurality of elements arranged to transmit an acoustic beam, to receive an acoustic echo reflected from the object to be inspected, and to output an analog element signal according to the received acoustic echo, the program causing the computer to execute:
a transmission step of using two or more elements among the plurality of elements of the probe as a transmission element and making the probe transmit the acoustic beam multiple times so as to form a predetermined transmission focal point;
a reception time of receiving an acoustic echo corresponding to each transmission of the acoustic beam with two or more elements among the plurality of elements as a reception element and outputting an analog element signal;
an A/D conversion step of performing A/D conversion on the analog element signal to generate first element data as a digital element signal;

a phasing addition step of performing phasing addition on the respective pieces of generated first element data with at least two lines as a center to generate at least two pieces of first reception data for each piece of first element data;

a reception data storage step of storing a plurality of pieces of first reception data generated in the phasing addition step;

a data acquisition step of reading two or more pieces of first reception data from the plurality of pieces of first reception data stored in the reception data storage step;

a reception data generation step of superimposing the two or more pieces of first reception data read in the data acquisition step to generate second reception data;

a processing condition setting step of setting the number of pieces of first reception data for use when generating the second reception data in the reception data generation step; and a mode switching step of switching between a measurement mode for performing transmission and reception of the acoustic wave and reproducing an image based on the received acoustic echo and a cine-reproduction mode for generating and reproducing an image using the plurality of pieces of first reception data stored in the memory without performing transmission and reception of the acoustic wave, wherein, in the cine-reproduction mode, the first reception data, the number of pieces of which is set in the processing condition setting step, is read from the memory in the data acquisition step, and the read first reception data is superimposed to generate the second reception data in the reception data generation step.

* * * * *